United States Patent
Kutyavin

(10) Patent No.: US 9,914,963 B2
(45) Date of Patent: Mar. 13, 2018

(54) METHODS AND COMPOSITIONS FOR DETECTION OF NUCLEIC ACIDS BASED ON STABILIZED OLIGONUCLEOTIDE PROBE COMPLEXES

(76) Inventor: Igor Kutyavin, Woodinville, WA (US)

( * ) Notice: Subject to any disclaimer, the term of this patent is extended or adjusted under 35 U.S.C. 154(b) by 1027 days.

(21) Appl. No.: 13/498,715

(22) PCT Filed: Sep. 15, 2010

(86) PCT No.: PCT/US2010/048995
§ 371 (c)(1),
(2), (4) Date: Jun. 13, 2012

(87) PCT Pub. No.: WO2011/037802
PCT Pub. Date: Mar. 31, 2011

(65) Prior Publication Data
US 2012/0252692 A1    Oct. 4, 2012

Related U.S. Application Data

(60) Provisional application No. 61/246,231, filed on Sep. 28, 2009.

(51) Int. Cl.
*C12Q 1/68* (2006.01)
(52) U.S. Cl.
CPC .................................. *C12Q 1/6853* (2013.01)
(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,683,195 A | 7/1987 | Mullis et al. |
| 4,683,202 A | 7/1987 | Mullis |
| 4,876,187 A | 10/1989 | Duck et al. |
| 5,011,769 A | 4/1991 | Duck et al. |
| 5,118,801 A | 6/1992 | Lizardi et al. |
| 5,210,015 A | 5/1993 | Gelfand et al. |
| 5,234,809 A | 8/1993 | Boom et al. |
| 5,270,184 A | 12/1993 | Walker et al. |
| 5,403,711 A | 4/1995 | Walder et al. |
| 5,422,253 A | 6/1995 | Dahlberg et al. |
| 5,487,972 A | 1/1996 | Gelfand et al. |
| 5,648,211 A | 7/1997 | Fraiser et al. |
| 5,691,142 A | 11/1997 | Dahlberg et al. |
| 5,712,124 A | 1/1998 | Walker |
| 5,723,591 A | 3/1998 | Livak et al. |
| 5,801,155 A | 9/1998 | Kutyavin et al. |
| 5,824,517 A | 10/1998 | Cleuziat et al. |
| 5,837,450 A | 11/1998 | Dahlberg et al. |
| 5,854,033 A | 12/1998 | Lizardi |
| 6,063,603 A | 5/2000 | Davey et al. |
| 6,127,121 A * | 10/2000 | Meyer, Jr. ............ C12Q 1/6818 435/6.11 |
| 6,140,496 A | 10/2000 | Benner |
| 6,251,639 B1 | 1/2001 | Kurn |
| 6,210,884 B1 | 4/2001 | Lizardi |
| 6,410,278 B1 | 6/2002 | Notomi et al. |
| 6,432,642 B1 | 8/2002 | Livak et al. |
| 6,492,346 B1 * | 12/2002 | Hedgpeth et al. ........... 514/44 R |
| 6,670,461 B1 | 12/2003 | Wengel et al. |
| 7,252,940 B2 | 8/2007 | Kutyavin et al. |
| 8,349,556 B2 * | 1/2013 | Kutyavin ....................... 435/6.1 |
| 2002/0034747 A1 * | 3/2002 | Bruchez, Jr. ............. B82Y 5/00 435/6.11 |

(Continued)

FOREIGN PATENT DOCUMENTS

EP        1312682       5/2003
WO    WO 2006/125267   11/2006

(Continued)

OTHER PUBLICATIONS

Ahmad Al, Ghasemi JB. New FRET primers for quantitative real-time PCR. Anal Bioanal Chem. Apr. 2007; 387(8):2737-43. Epub Feb. 17, 2007.*

(Continued)

*Primary Examiner* — Angela M Bertagna
*Assistant Examiner* — Olayinka Oyeyemi
(74) *Attorney, Agent, or Firm* — Barry L. Davison; Davis Wright Tremaine LLP

(57) ABSTRACT

Provided are nucleic acid detection methods wherein targeted primer extension or products or amplification products incorporate a probe-anchoring modification introduced using a primer incorporating a probe-anchoring primer modification, wherein oligonucleotide detection probes incorporate a probe-anchoring probe modification, the primers and probes designed to place the binding site of the oligonucleotide probe proximate to the probe-anchoring primer modification in the detected target sequence. The probe-anchoring modifications of the probe and the primer-extension product form a stabilized complex comprising a detectible duplex of the probe with the detected target sequence. In certain aspects, the probe-anchoring modified primer also incorporates a probe-directing sequence. The methods allow use of exceptionally short oligonucleotide probes (e.g., 10-mer and shorter) enabling establishment of a complete probe inventory or universal library containing a probe complementary to any target nucleic acid sequence. Real-time and post-amplification detection methods are provided, along with detection kits.

18 Claims, 13 Drawing Sheets

(56) References Cited

U.S. PATENT DOCUMENTS

| | | |
|---|---|---|
| 2003/0138800 A1 | 7/2003 | Van Ness et al. |
| 2004/0058322 A1* | 3/2004 | Hedgpeth et al. ............... 435/6 |
| 2007/0059752 A1 | 3/2007 | Cook |

FOREIGN PATENT DOCUMENTS

| | | | |
|---|---|---|---|
| WO | WO 2007/127992 | 11/2007 | |
| WO | WO 2007/127999 | 11/2007 | |
| WO | WO 2008/086381 | 7/2008 | |
| WO | WO2008/152144 | * 12/2008 | ............... C12Q 1/68 |
| WO | WO 2008/152144 | 12/2008 | |
| WO | WO 2009/042291 | 4/2009 | |

OTHER PUBLICATIONS

Kutyavin IV, Afonina IA, Mills A, Gorn VV, Lukhtanov EA, Belousov ES, Singer MJ, Walburger DK, Lokhov SG, Gall AA, Dempcy R, Reed MW, Meyer RB, Hedgpeth J. 3'-minor groove binder-DNA probes increase sequence specificity at PCR extension temperatures. Nucleic Acids Res. Jan. 15, 2000; 28(2):655-61.*

Kutyavin IV. New approach to real-time nucleic acids detection: folding polymerase chain reaction amplicons into a secondary structure to improve cleavage of Forster resonance energy transfer probes in 5'-nuclease assays. Nucleic Acids Res. Mar. 2010; 38(5):e29.pp. 1-12. Epub Dec. 7, 2009.*

Lehmann et al., English translation of WO2008/152144, published Dec. 18, 2008.*

Thibault V, Pichoud C, Mullen C, Rhoads J, Smith JB, Bitbol A, Thamm S, Zoulim F. Characterization of a new sensitive PCR assay for quantification of viral DNA isolated from patients with hepatitis B virus infections. J Clin Microbiol. Dec. 2007; 45(12):3948-53. Epub Oct. 17, 2007.*

Zhang Y, Zhang D, Li W, Chen J, Peng Y, Cao W. A novel real-time quantitative PCR method using attached universal template probe. Nucleic Acids Res. Oct. 15, 2003; 31(20):e123. pp. 1-8.*

Whitcombe D, Theaker J, Guy SP, Brown T, Little S. Detection of PCR products using self-probing amplicons and fluorescence. Nat Biotechnol. Aug. 1999; 17(8):804-7.*

Whitcombe D, Theaker J, Guy SP, Brown T, Little S. Detection of PCR products using self-probing amplicons and fluorescence. Nat Biotechnol. Aug. 1999; 17(8):804-7. (Year: 1999).*

Afonina LA. et al. "Minor Groove Binder-Conjugated DNA Probes for Quantitative DNA Detection by Hybridization-Triggered Fluorescence." (Apr. 2002) BioTechniques, vol. 32, pp. 940-949.

An L. et al. "Characterization of a Thermostable UvrD Helicase and Its Participation in Helicase-dependent Amplification." (2005) The Journal of Biological Chemistry. vol. 280, pp. 28952-28958.

Asseline U. et al. "Nucleic acid-binding molecules with high affinity and base sequence specificity: Intercalating agents covalently linked to oligodeoxynucleotides." (Feb. 1984) Proc. Natl. Acad. Sci. USA, vol. 81, pp. 3297-3301.

Ausubel F.M et al, eds. "Hybridization Analysis of DNA Blots." (1993) Current Protocols in Molecular Biology, vol. 1, Chapter 2, Section I, pp. 2.10.1-2.10.16. John Wiley & Sons, New York.

Beaucage S. L., Caruthers M. H. "Deoxynucleoside Phosphoramidites—a New Class of Key Intermediates for Deoxypolynucleotide Synthesis." (1981) Tetrahedron Letters. vol. 22, pp. 1859-1862.

Breslauer K.J. et al. "Predicting DNA duplex stability from the base sequence." (1986) Proc. Natl. Acad. Sci. USA. vol. 83, pp. 3746-3750.

Brown E.L. et al. "Chemical Synthesis and Cloning of a Tyrosine tRNA Gene." (1979) Methods in Enzymology. vol. 68, pp. 109-151.

Didenko V.V. "DNA Probes Using Fluorescence Resonance Energy Transfer (FRET): Designs and Applications." (Nov. 2001) BioTechniques. vol. 31, No. 5, pp. 1106-1121.

Eftink M.R. "Fluorescence quenching: theory and applications." (1991). In Lakowicz J.R. (ed.), Topics in Fluorescence Spectroscopy. Plenum Press, New York, vol. 2, pp. 53-126.

Egholm M. et al. "PNA hybridizes to complementary oligonucleotides obeying the Watson-Crick hydrogen-bonding rules." (1993) Nature. vol. 365, pp. 566-568.

Fong W. et al. "Rapid Solid-Phase Immunoassay for Detectoin of Methicillin-Resistant Staphylococcus aureus Using Cycling Probe Technology." (2000) Journal of Clinical Microbiology. vol. 38, No. 7, pp. 2525-2529.

Forster T. "Delocalized excitation and excitation transfer." (1965). In Sinanoglu, O. (ed.), Modem Quantum Chemistry, Istanbul Lectures, part III. Academic Press, New York, pp. 93-137.

Harvey J.J. et al. :Characterization and applications of CataCleave probe in real-time detection assays. (2004) Analytical Biochemistry. vol. 333, pp. 246-255.

Heller M.J. and Morrison L.E. "Chemiluminescent and fluorescent probes for DNA hybridization Systems." (1985). In Kingsbury, D.T. and Falkow, S. (eds.), Rapid Detection and Identification of Infectious Agents. Academic Press, New York, pp. 245-256.

Kaiser, et al. A Comparison of Eubacterial and Archaeal Structruespecific 5'-Exonucleases. (1999). The Journal of Biological Chemistry. vol. 274, No. 30, pp. 21387-21394.

Kutyavin I.V. et al. "A novel endonuclease IV post-PCR genotyping system." (2006) Nucleic Acids Research. vol. 34, pp. e128.1-e128-9.

Kutyavin, I.V. "New approach to real-time nucleic acids detection: Folding polymerase chain reaction amplicons into a secondary structure to improve cleavage of Forster resonance energy transfer probes in 5'-nuclease assays." (May 1, 2010). Nucleic Acids Research, Information Retrieval Ltd. vol. 38, No. 5, pp. e29.1-e29.12.

Kutyavin, I.V. "Use of extremely short Forster resonance energy transfer probes in real-time polymerase chain reaction." (2013). Nucleic Acids Research. vol. 41, No. 20, pp. e191.1-e.191.10.

Lebedev Y. et al. "Oligonucleaotides containing 2-aminoadenine and 5-methylcytosine are more effective as primers for PCR amplication than their nonmodified counterparts." (1996). Genetic Analysis. vol. 13, pp. 15-21.

Lyamichev V. et al. "Structure-Specific Endonucleolytic Cleavage of Nucleic Acids by Eubacterial DNA Polymerases." (1993) Science. vol. 260, pp. 778-783.

Mackay I.M., et al. "Survey and Summary: Real-time PCR in virology." (2002) Nucleic Acids Research. vol. 30, pp. 1292-1305.

Mackay J., and Landt O. "Real-Time PCR Fluorescent Chemistries." (2007) Methods in Molecular Biology, vol. 353, pp. 237-261.

Miller S.A., et al. "A simple salting out procedure for extracting DNA from human nucleated cells." (1988) Nucleic Acids Research. vol. 16, No. 3, p. 1215.

Narang S.A., et al. "Improved Phosphotriester Method for the Synthesis of Gene Fragments." (1979). Methods in Enzymology. vol. 68, pp. 90-98.

Oehlenschlager F. et al. "Detection of HIV-1 RNA by nucleic acid sequence-based amplification combined with fluorescence correlation spectroscopy." (1996). Proc. Natl. Acad. Sci. USA, vol. 93, pp. 12811-12816.

Robelek R., et al. "Multiplexed Hybridization Detection of Quantum Dot-Conjugated DNA Sequences Using Surface Plasmon Enhanced Fluorescence Microscopy and Spectrometry." 2004. Analytical Chemistry. vol. 76, No. 20, pp. 6160-6165.

Santalucia J. Jr. "A unified view of polymer, dumbbell, and oligonucleotide DNA nearest-neighbor thermodynamics." (1998). Proc. Natl. Acad. Sci. USA. vol. 95, pp. 1460-1465.

Van Ness J. et al. "Isothermal reactions for the amplification of oligonucleotides." (2003) Proc. Natl. Acad. Sci. USA. vol. 100, pp. 4504-4509.

Vincent M., et al. "Helicase-dependent isothermal DNA amplification." (2004) EMBO reports. vol. 5, pp. 795-800.

Walker G.T., et al. "DNA detection by strand displacement amplification and fluorescence polarization with signal enhancement using a DNA binding protein." (1996). Nucleic Acids Research. vol. 24, No. 2, pp. 348-353.

(56) References Cited

OTHER PUBLICATIONS

Walsh P.S., et al. "Chelex® 100 as a Medium for Simple Extraction of DNA for PCR-Based Typing from Forensic Material." (1991) *Biotechniques*. vol. 10, No. 4, pp. 506-513.

* cited by examiner

METHODS AND COMPOSITIONS FOR DETECTION OF NUCLEIC ACIDS BASED ON STABILIZED OLIGONUCLEOTIDE PROBE COMPLEXES

CROSS-REFERENCE TO RELATED APPLICATIONS

This application is the United States national phase, under 35 U.S.C. § 371, of International Patent Application No. PCT/US2010/048995, filed 15 Sep. 2010, which claims the benefit of priority to U.S. Provisional Patent Application Ser. No. 61/246,231, filed 28 Sep. 2009 and entitled "METHODS AND COMPOSITIONS FOR DETECTION OF NUCLEIC ACIDS BASED ON STABILIZED OLIGONUCLEOTIDE PROBE COMPLEXES," both of which are incorporated herein by reference in their entirety.

STATEMENT REGARDING FEDERALLY-SPONSORED RESEARCH

Not Applicable.

SEQUENCE LISTING

A Sequence Listing comprising SEQ ID NOS:1-13, has been provided in computer readable form (.txt) as part of this application, and is incorporated by reference herein in its entirety as part of this application.

FIELD OF THE INVENTION

Aspects of the invention relate generally to improved nucleic acid detection methods, and particularly to amplification-based nucleic acid detection methods wherein target amplification products incorporate special modifications providing for improvement of nucleic acid detection using stabilized oligonucleotide probe complexes.

BACKGROUND

Early recognition of pathogens and genetic diseases, and susceptibility and/or predisposition thereto is vitally important in healthcare and, at least in part, depends on the ability to detect nucleic acids with accuracy and sensitivity. Not surprisingly, DNA and RNA detection methods are now routinely used for forensic, paternity, military, environmental and other testing applications. Although some highly sensitive technologies for direct nucleic acid detection are currently under development, amplification of targeted sequences is an important component of many DNA detection systems today. Most sensitive and accurate methods are based on oligonucleotide probe detection. An oligonucleotide sequence can be chosen to form a perfect match duplex with any predetermined site of an amplified polynucleotide sequence of interest. This complementary duplex can then be detected indicating the presence of the targeted nucleic acid in the reaction mixture. In many methods based on nucleic acids amplification, the oligonucleotide probes do not need to be longer than 6-10-mers to provide for explicit detection of polynucleotide sequences of interest. Probes of this length are sequence-specific within the context of amplicons that are 100-500 base pairs long. Use of the short probes improves many aspects of the detection process and can be particularly effective, for example, in enhancing the detection signal while reducing the signal background and unambiguously identifying target polymorphic variations as small as single nucleotide polymorphism. Moreover, the 10-mer and shorter oligonucleotide probes provide opportunity to establish a complete probe inventory, a universal probe library which would always contain a complementary probe for detection of any given sequence of any target nucleic acid.

However, the probe-target duplex needs to be stable enough to enable the detection by a particular method. Generally, duplex stability depends on the duplex length and base pair composition. Detection of A/T-rich sequences is notoriously difficult due to the thermodynamic instability of A-T base pair relative to the G-C pair. Moreover, many currently used detection methods, for example, those based on the real time polymerase chain reaction (PCR) (see, e.g., U.S. Pat. Nos. 4,683,195 and 4,683,202 to Mullis K. B., 1987), are performed at temperatures exceeding 50-60° C. In these aspects, the probes commonly needs to be 18-20-mers or longer oligonucleotides in order to address both, the natural sequence variety of nucleic acids and the elevated temperatures of the detection methods used. A number of technologies have been proposed to enhance the oligonucleotides hybridization properties. The examples include base-modified (Lebedev Y. et al, 1996) and sugar-modified nucleotide analogs like LNA (Wengel J., Nielsen P., 2003) and PNA (Egholm M. et al, 1993), duplex-stabilizing tails like minor groove binders (Kutyavin I. V. et al, 1998) and intercalators (e.g., Asseline U. et al, 1984). With regard to the PCR-based methods, use of these chemical modifications allows to reduce the probe average length to ~12-18-mer oligonucleotides. However, this length range is still out of reach of a reasonably-sized universal library of the detection probes.

There is therefore, a pronounced need in the art for more efficient and versatile methods of nucleic acids detection that can employ very short oligonucleotide probes, particularly shorter than <8-mers, regardless of the nucleotide composition of the detected nucleic acids of interest.

BRIEF DESCRIPTION OF THE DRAWINGS

FIG. 8A shows an example of PCR-based method wherein the probe target-specific cleavage is provided by a 5'-nuclease during strand elongation. In this particular case, Taq polymerase cleaves the probe that is hybridized downstream from a primer site, releasing the reporter dye (F) from the quencher (Q) and providing for the detection. In the diagram B, the target specific cleavage is provided by Endonuclease V. A FRET probe incorporates 5'-terminal deoxyinosine nucleoside to direct the endonuclease cleavage predominantly at the internucleotide linkage shown by arrow. Deoxyinosine can be located at the first, second or third nucleotide position from the 5'-end of the endo-V-cleavable oligonucleotide probe. The diagram C illustrates an example of the methods of FIG. 6. A probe cleavable site for Endonuclease IV is formed by a FRET probe duplex and a cleavage-enhancing duplex provided by the amplicon that folds into a stem-loop structure at the 5'-end. The duplexes are separated by one unhybridized target nucleotide for the optimal assay performance.

FIG. 11A shows the results of the fluorescence signal monitoring for 6 and 7-mer FRET-probes in detecting of the PCR-preamplified target nucleic acid (SEQ ID NO:1) at 50° C. FIG. 11B illustrates for these probes the dependence of the initial rate of cleavage vs. detection temperature. FIGS. 11C and 11D are the results of the post-PCR detection of the matched (SEQ ID NO:1) and mismatched (SEQ ID NO:2 and SEQ ID NO:3) target sequences by 6 and 7-mer anchored probes at the temperatures of optimal performance, 47° C. and 56° C. as indicated in each case. Each real-time curve shown in FIG. 11

FIGS. 12A and 12B show, according to particular exemplary aspects of the present invention, detection of a β2-macroglobulin target sequence (SEQ ID NO:1) in a real time PCR assay using 6-mer (SEQ ID NO:10) and 7-mer (SEQ ID NO:11) FRET probes, respectively. The reaction compositions were identical to those in FIG. 11. In both cases, the target sequences were amplified using the 5'-flap forward primer (SEQ ID NO:6). The 5'-flap reverse primer (SEQ ID NO:7) was used in detection reactions with the 6-mer FRET probe (SEQ ID NO:10) whereas 5'-flap reverse primer (SEQ ID NO:8) was used with the 7-mer FRET probe (SEQ ID NO:11). The following PCR profile was applied in these experiments: (95° C. 2 min)→(95° C. 10 sec→56° C. 70 sec→70° C. 30 sec)$_{55}$ wherein underlined is the fluorescence monitoring stage. As indicated in the diagrams A and B, the low or no signal fluorescence curves represent the control experiments wherein, in otherwise identical reactions, one of the 5'-flap primers was replaced by a regular forward (SEQ ID NO:4) or regular reverse (SEQ ID NO:5) primer. One of the no-signal fluorescence curves represent an experiment wherein the 6 and 7-mer probes incorporating the probe-anchoring sequence were replaced respectively by conventionally designed probes (SEQ ID NO:12 and SEQ ID NO:13) of the same length and composition but lacking the probe-anchoring sequence. For comparison of the relative performance of the invention methods with other art recognized technologies, FIG. 12C shows real time fluorescence monitoring obtained in a Taqman™ assay. This assay was detecting the same target sequence (SEQ ID NO:1) but using a 22-mer FRET probe (SEQ ID NO:9), regular forward (SEQ ID NO:4) and regular reverse (SEQ ID NO:5) primers. The structures of the probes, primers and DNA targets are shown in FIG. 10. Detailed description of the experiments is provided herein in working Example 3. All diagrams A, B and C are shown in the same fluorescence scale.

FIGS. 13A and 13B show, according to particular exemplary aspects of the present invention, detection of a match β2-macroglobulin target sequence (SEQ ID NO:1) and two mismatched (SEQ ID NO:2 and SEQ ID NO:3) target sequences in a real time PCR assay using 6-mer (SEQ ID NO:10) and 7-mer (SEQ ID NO:11) FRET probes, respectively. Except the target variations, the reaction compositions and PCR profile were identical to those described in FIG. 12. The structures of the probes, primers and DNA targets are shown in FIG. 10. Detailed description of the experiments is provided herein in working Example 4. Both diagrams A and B are shown in the same fluorescence scale.

DETAILED DESCRIPTION OF EXEMPLARY EMBODIMENTS

Figure 1:
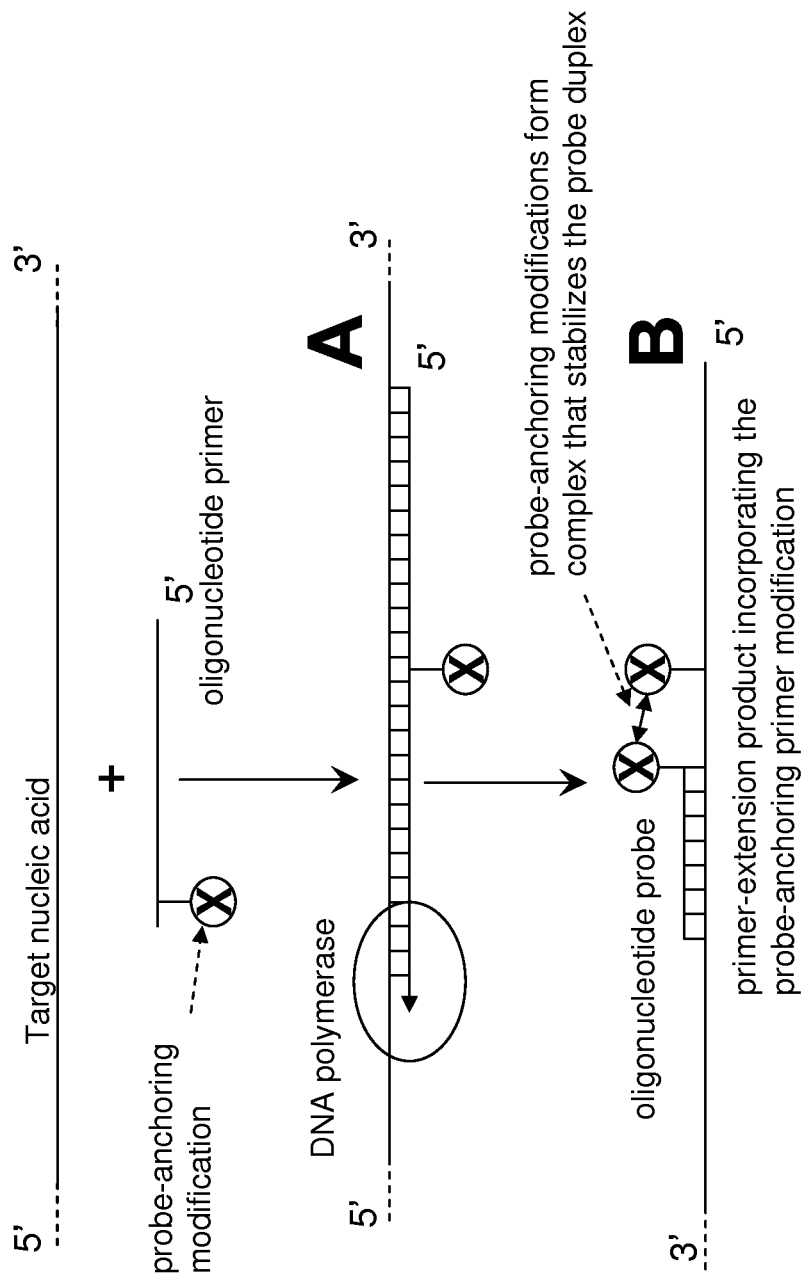
FIG. 1 illustrates particular exemplary aspects of the present invention in detecting target nucleic acids. An oligonucleotide primer is complementary to a target nucleic acid and incorporates a probe-anchoring (PA) modification X that is conjugated to the primer at or nearby the 3'-end. Under suitable reaction conditions and reagents, the primer hybridizes to the target nucleic acid, and DNA polymerase extends the primer synthesizing a primer-extension product which incorporates the PA modification (stage A), after which the primer-extension product is rendered single-stranded. An oligonucleotide probe that also comprises a PA modification hybridizes to the primer-extension product (stage B). The PA modifications of the probe and the primer-extension product interact and this leads to stabilization of the probe duplex providing for the duplex detection.

Terms and symbols of biochemistry, nucleic acid chemistry, molecular biology and molecular genetics used herein follow those of standard treaties and texts in the field (e.g., Sambrook J. et al, 1989; Kornberg A. and Baker T., 1992; Gait M. J., ed., 1984; Lehninger A. L., 1975; Eckstein F., ed., 1991, and the like). To facilitate understanding of particular exemplary aspects of the invention, a number of terms are discussed below.

Particular aspects of the present invention provide methods for detecting a target nucleic acid in a test sample comprising: providing a reaction mixture comprising a target nucleic acid having a respective target nucleic acid sequence, an oligonucleotide primer complementary to the target nucleic acid sequence and having at least one probe-anchoring primer modification, and a DNA polymerase suitable for primer extension of the hybridized primer; incubating the reaction mixture in the presence of suitable reagents and under reaction conditions suitable to support primer hybridization and DNA polymerase-mediated primer extension, to provide for a respective primer-extension product incorporating the probe-anchoring primer modification; rendering the primer-extension product single stranded; providing, in the reaction mixture, an oligonucleotide probe comprising at least one probe-anchoring probe modification, the probe complementary to the primer-extension product incorporating the at least one probe-anchoring primer modification; incubating the reaction mixture under reaction conditions suitable to support hybridization of the probe to the primer-extension product to provide a stabilized probe: primer-extension product duplex, wherein the respective at least one probe-anchoring modifications of the probe and the primer-extension product form a complex that stabilizes the duplex; and detecting the duplex, wherein the presence of the duplex is indicative of the presence of the target nucleic acid sequence in the reaction mixture.

In particular aspects, "sample" refers to any substance containing or presumed to contain a nucleic acid of interest. The term "sample" thus includes but is not limited to a sample of nucleic acid, cell, organism, tissue, fluid, or substance including but not limited to, for example, plasma, serum, urine, tears, stool, respiratory and genitourinary tracts, saliva, semen, fragments of different organs, tissue, blood cells, samples of in vitro cell cultures, isolates from natural sources such as drinking water, microbial specimens, and objects or specimens that have been suspected to contain nucleic acid molecules.

In particular aspects, "target nucleic acid" or "nucleic acid of interest" refers to a nucleic acid or a fragment of nucleic that is to be amplified and/or detected using methods of the present invention. Nucleic acids of interest can be of any size and sequence; e.g. as big as genomic DNA. Preferably, the nucleic acid is of a size that provides for detection and/or amplification thereof. Two or more target nucleic acids can be fragments or portions of the same nucleic acid molecule. As used herein, target nucleic acids are different if they differ in nucleotide sequence by at least one nucleotide. In this aspect, the invention may be used to detect "polymorphic variations" wherein, for example, two nucleic acids of interest have significant degree of identity in the sequence but differ by only a few nucleotides (e.g. insertions, deletions) or by a single nucleotide, or single nucleotide polymorphism (SNP). Target nucleic acids can be single-stranded or double-stranded. When nucleic acid of interest is double-stranded or presumed to be double-stranded, the term "target nucleic acid" refers to a specific sequence in either strand of double-stranded nucleic acid. Therefore, the full complement to any single stranded nucleic acid of interest is treated herein as the same (or complementary) target nucleic acid. In certain aspects, target nucleic acids of the invention comprise polynucleotides comprising natural and/or modified nucleotides, if the presence of these structural modifications is beneficial for the detection by the methods of the invention, e.g. duplex-stabilizing base-modified nucleotide to enhance hybridization properties of the primers and probes according to the methods of Kutyavin I. V. (2007b).

Target nucleic acids, or nucleic acids of interest are preferably single-stranded. The detection reaction of the invention is initiated when an oligonucleotide primer complementary to the target nucleic acid sequence hybridizes to a complementary single-stranded nucleic acid forming a double-stranded substrate that is recognized and extended by a DNA polymerase. When target nucleic acids are double-stranded, they are rendered single stranded by any physical, chemical or biological approach before applying the methods of the invention. For example, double-stranded nucleic acid can be denatured at elevated temperature, e.g. 90-95° C. The target nucleic acids may be derived from any organism or other source, including but not limited to prokaryotes, eukaryotes, plants, animals, and viruses, as well as synthetic nucleic acids. The target nucleic acids may be DNA, RNA, and/or variants thereof. Nucleic acids of interest can be isolated and purified from the sample sources before applying methods of the present invention. Preferably, the target nucleic acids are sufficiently free of proteins and any other substances interfering with primer-extension and detection reactions. Many methods are available for the isolation and purification of nucleic acids of interest including commercial kits and specialty instruments. For example, nucleic acids can be isolated using organic extraction with a phenol/chloroform reagent followed by ethanol precipitation (Ausubel F. M et al, eds., 1993). Solid phase adsorption method (Walsh P. S. et al, 1991; Boom W. R. et al, 1993) and salt-induced DNA precipitation (Miller S. A. et al, 1988) are yet other known approaches to purify nucleic acids. In a preferred embodiment, the target nucleic acid is DNA. In another embodiment, the target nucleic is RNA. Prior to applying the methods of the invention, a DNA copy (cDNA) of target RNA can be obtained using an oligonucleotide primer that hybridize to the target RNA, and extending of this primer in the presence of a reverse transcriptase and nucleoside 5'-triphosphates. The resulting DNA/RNA heteroduplex can then be rendered single-stranded using techniques known in the art, for example, denaturation at elevated temperatures. Alternatively, the RNA strand may be degraded in presence of RNase H nuclease.

The term "reaction mixture" generally means a water solution containing all the necessary reactants including oligonucleotide components, enzymes, nucleoside triphosphates, ions like magnesium and other reaction components for performing an amplification or detection reaction of the invention or both. Magnesium ion is preferably present in the reaction mixture because it enables catalytic activity of DNA polymerases and also nucleases in the methods based on cleavable-probes. "Polynucleotide" and "oligonucleotide" are used herein interchangeably and each means a linear polymer of nucleotide monomers. Polynucleotides typically range in size from a few monomeric units, e.g. 5-40, when they are usually referred to as "oligonucleotides," to several thousand monomeric units. The exact size will depend on many factors, which in turn depends on the ultimate function or use of the oligonucleotide. The oligonucleotides may be generated in any manner, including chemical synthesis, DNA replication, reverse transcription, or a combination thereof. Whenever a polynucleotide or oligonucleotide is represented by a sequence of letters, for example, "CCGTATG," it is understood herein, unless otherwise specified in the text, that the nucleotides are in 5'→3' order from left to right and that "A" denotes deoxyadenosine, "C" denotes deoxycytidine, "G" denotes deoxyguanosine, and "T" denotes deoxythymidine. Usually DNA polynucleotides comprise these four deoxyribonucleosides linked by phosphodiester linkage whereas RNA comprises uridine ("U") in place of "T" for the ribose counterparts.

The term "oligonucleotide component" refers to any molecule of polynucleotide nature that is required or helpful in conducting either amplification or detection reaction of the invention or both. Oligonucleotide components include but not limited to primers, probes, hybridization and cleavage enhancers, effectors, etc. Oligonucleotide components can be labeled or have structural modifications of any kind. The terms "oligonucleotide primer" and/or "primer" refer to a single-stranded DNA or RNA molecule that hybridizes to a target nucleic acid and primes enzymatic synthesis of a second nucleic acid strand in presence of a DNA polymerase. In this case, as used herein, the target nucleic acid "serves as a template" for the oligonucleotide primer. As used herein, the term an "oligonucleotide probe" or "probe" refers to an oligonucleotide component which is used to detect nucleic acids of interest. These terms encompasses various derivative forms such as "hybridization-triggered probe," "fluorescent probe," "FRET probe," etc.

"Hybridizing," "hybridization" or "annealing' refers to a process of interaction between two or more oligo- or polynucleotides forming a complementary complex through base pairing which is most commonly a duplex. The stability of a nucleic acid duplex is measured by the melting temperature. "Melting temperature" or "Tm" means the temperature at which a complementary duplex of nucleic acids, usually double-stranded, becomes half dissociated into single strands. These terms are also used in describing stabilities of secondary structures wherein two or more fragments of the same polynucleotide interact in a complementary fashion with each other forming duplexes, usually hairpin-like structures. "Hybridization properties" of a polynucleotide means an ability of this polynucleotide or its fragment to form a sequence specific duplex with another complementary polynucleotide or its fragment. "Hybridization properties" is also used herein as a general term in describing the complementary duplex stability. In this aspect, "hybridization properties" are similar in use to "melting temperature" or "Tm." "Improved" or "enhanced hybridization properties" of a polynucleotide refers to an increase in stability of a duplex of this polynucleotide with its complementary sequence due to any means including but not limited to a change in reaction conditions such as pH, salt concentration and composition, for example, an increase in magnesium ion concentration, presence of duplex stabilizing agents such as intercalators or minor groove binders, etc., conjugated or not. The hybridization properties of a polynucleotide or oligonucleotide can also be altered by an increase or decrease in polynucleotide or oligonucleotide length. The cause of the hybridization property enhancement is generally defined herein in context.

In particular aspects, the terms "complementary" or "complementarity" are used herein in reference to the polynucleotides base-pairing rules. Double-stranded DNA, for example, consists of base pairs wherein, for example, G forms a three hydrogen bond couple, or pairs with C, and A forms a two hydrogen bond complex, or pairs with T, and it is regarded that G is complementary to C, and A is complementary to T. In this sense, for example, an oligonucleotide 5'-GATTTC-3' is complementary to the sequence 3'-CTAAAG-5'. Complementarity may be "partial" or "complete." For example, as referred to herein the phrase "a probe (or a primer) that is complementary to the target nucleic acid," the term "complementary" incorporates both partial and complete complementarity. In partial complementarity, only some of the nucleic acids bases are matched according to the base pairing rules. The degree of complementarity between nucleic acid strands has significant effects on the strength of hybridization between nucleic acids. This is particularly important in performing amplification and detection reactions that depend upon nucleic acids binding. The terms may also be used in reference to individual nucleotides and oligonucleotide sequences within the context of polynucleotides. As used herein, the terms "complementary" or "complementarity" refer to the most common type of complementarity in nucleic acids, namely Watson-Crick base pairing as described above, although the primers, probes, oligonucleotide components and amplification products of the invention may participate, including an intelligent design, in other types of "non-canonical" pairings like Hoogsteen, wobble and G-T mismatch pairing.

In general, the term "design" in the context of the methods and/or oligonucleotides, etc., has broad meaning, and in certain respects is equivalent to the term "selection." For example, the terms "oligonucleotide design," "primer design," "probe design" can mean or encompass selection of a particular, or sometimes not necessarily a particular, oligonucleotide structure including the nucleotide sequence and structural modifications (e.g., labels, modified nucleotides, linkers, etc.). The term "system design" generally incorporates the terms "oligonucleotide design", "primer design", "probe design" and also refers to relative orientation and/or location of the oligonucleotide components and/or their binding sites within the target nucleic acids. In these aspects, the term "assay design" relates to the selection of any, sometimes not necessarily to a particular, methods including all reaction conditions (e.g. temperature, salt, pH, enzymes, oligonucleotide component concentrations, etc.), structural parameters (e.g. length and position of primers and probes, design of specialty sequences, etc.) and assay derivative forms (e.g. post-amplification, real-time, immobilized, FRET detection schemes, etc.) chosen to amplify and/or to detect the nucleic acids of interest. As used herein, "detection assay" or "assay" refers a reaction or chain of reactions that are performed to detect nucleic acids of interest. The assay may comprise multiple stages including amplification and detection reactions performed consequently or in real-time, nucleic acid isolation and intermediate purification stages, immobilization, labeling, etc. The terms "detection assay" or "assay" encompass a variety of derivative forms of the methods of the invention, including but not limited to, a "post-amplification assay" when the detection is performed after the amplification stage, a "real-time assay" when the amplification and detection are performed simultaneously, a "FRET assay" when the detection is based using a FRET effect, "immobilized assay" when one of either amplification or detection oligonucleotide components or an amplification product is immobilized on solid support, and the like.

Methods of the invention are based on use of an oligonucleotide probe comprising at least one probe-anchoring modification. The probe is complementary to a primer-extension product which also incorporates at least one probe-anchoring modification. Hybridization of the probe to the primer-extension product provides for a duplex between the probe and primer-extension product, wherein the respective probe-anchoring modifications of the probe and the primer-extension product form a complex and the complex stabilizes the probe:primer-extension product duplex. In this aspect, the term "probe-anchoring" or "PA modification" refers to any structural entity (modification) that is capable of forming a complex with another structural entity and, when these entities are incorporated respectively into a probe and a primer-extension product, the complex stabilizes the complementary duplex between the probe and the primer-extension product. The term "complex" usually refers to an interaction between two PA modifications. In particular aspects, the PA modifications can comprise complementary nucleotide sequences forming a duplex. In this aspect, the term "complex" may incorporate the term "duplex." The probe-anchoring modifications can comprise of natural and unnatural compounds or structural modifications of any kind.

The term "structural modifications" refers to any chemical substances such as atoms, moieties, residues, polymers, linkers or nucleotide analogs that are usually of a synthetic nature, and which are not commonly present in natural nucleic acids. "Duplex-stabilizing modifications" refer to structural modifications, the presence of which in double-stranded nucleic acids provides a duplex-stabilizing effect when compared in thermal stability, usually measured as Tm, with respective nucleic acid duplexes that have no structural modification and comprised natural nucleotides. Duplex-stabilizing modifications are structural modifications that are most commonly applied in synthesis of probes and primers and represented by modified nucleotides and "tails" like intercalators and minor groove binders.

The primer-extension products are produced in methods of the invention by DNA-polymerase-assisted extension of the primers that incorporate the PA modification and hybridize to the target nucleic acids. Generally, the probe:primer-extension product duplex is formed as close as possible to the primer sequence incorporated into the primer-extension product to provide a stable complex between the corresponding PA modifications. A PA modification can be located anywhere within the primer. For example, FIG. 1 illustrates particular preferred methods when probe-anchoring (PA) modification is conjugated to the primer at or nearby the 3'-end. When the incorporated primer sequence is close to the probe:primer-extension product duplex, this places the PA modifications in proximity to interact and provide stable complex which, in turn, stabilizes the probe: primer-extension product duplex. The PA-modified primer is incorporated into the extension product and this determines the location of a PA modification within the primer-extension product: at or near the 5'-end. Unless the PA modification is a nucleotide sequence, it may not be introduced to or near the 3'-end of the primer-extension product. The PA modifications can comprise the natural nucleotide(s), modified nucleotide(s), intercalator, minor groove binder, specialty linker or a combination thereof. The terms "natural nucleosides" and "natural nucleotides" as used herein refer to four deoxynucleosides or deoxynucleotides respectively which may be commonly found in DNAs isolated from natural sources. Natural nucleosides (nucleotides) are deoxyadenosine, deoxycytidine, deoxyguanosine, and deoxythymidine. The term also encompasses their ribose counterparts, with uridine in place of thymidine. As used herein, the terms "unnatural nucleotides" or "modified nucleotides" refer to nucleotide analogs that are different in their structure from those natural nucleotides for DNA and RNA polymers. Some of the naturally occurring nucleic acids of interest may contain nucleotides that are structurally different from the natural nucleotides defined above, for example, DNAs of eukaryotes may incorporate 5-methylcytosine and tRNAs are notorious for harboring many nucleotide analogs. However, as used herein, the terms "unnatural nucleotides" or "modified nucleotides" encompasses these nucleotide modifications even though they can be found in natural sources. For example, ribothymidine and deoxyuridine are treated herein as unnatural nucleosides.

The complex formation between the PA modifications can be of any physical or chemical interaction including but not limited to the hydrophobic, stacking, ionic, hydrogen bond, covalent bond, complementary oligonucleotide interaction or a combination thereof. The PA primer modifications must not block the extension of the primer by DNA polymerase to produce the primer-extension product. In preferred aspects, the PA primer modifications also do not block synthesis of a complementary strand when the primer-extension products incorporating the PA modifications serve as a template. The PA modifications forming the complex can be identical or different. For example, the PA modifications may comprise cholesterol moieties that are of hydrophobic nature and in equivoques solutions form stable complex. The PA modifications may comprise minor groove binders that are hydrophobic and also usually flat molecules capable to interact through the molecular stacking. The detection system may be designed such as, according to the teaching of Kutyavin I. V. et al, 1998, the complex of two minor groove binders can bind to minor groove of the probe:primer-extension product duplex and effectively stabilize the duplex. The methods of the invention wherein the complex formation between the PA modifications leads to formation of a covalent bond can be especially effective in stabilizing the probe:primer-extension product duplex. The covalent bond formation can be reversible or irreversible. There are many methods established in the art, also known under a term "chemical ligation," that can be used to form covalent bonds between two PA modifications in aqueous solutions of the amplification and detection assays. Examples include but not limited to Schiff base formation (reversible); reaction of activated phosphates with amines: —O—PO$_2$—X+ NH2→—O—PO$_2$—NH—; phosphorotioates with bromo- or iodoalkyls: —O—PO$_2$—S$^-$+I—CH$_2$—→—O—PO$_2$—S—CH$_2$—; mercaptans with bromo- or iodoalkyls: —CH$_2$—SH+I—CH$_2$—→—CH$_2$—S—CH$_2$—; disulfide bond formation: —CH$_2$—SH+HS—CH$_2$—→—CH$_2$—S—S—CH$_2$—; and many other reactions as will be recognized in the art.

In particular embodiments, the PA modifications comprise nucleotide sequences. In this aspect, the probe and primer PA modifications are sequences that are complementary to each other and form a complementary duplex. The nucleotide sequences of the probe and primer PA modifications are preferably selected to avoid hybridization of these sequences with target nucleic acids, products of target amplification and oligonucleotide components. The probe-anchoring sequence design should also circumvent the sequence self-complementarity wherein a specific PA sequence can form duplex with itself (e.g. GGAATTCC). The PA sequence can be located at the 5'-end of the primer as this illustrated in FIG. 2. Although PA sequence may not be located at the 3'-end of the primer, it can be located at the middle or nearby the 3'-end, e.g. 3-5 bases away from the 3'-end, as this is exemplified in FIG. 3. Given the present teachings, those of ordinary skill in the art will appreciate that use of nucleotide sequences as PA modifications provides an advantage of forming the complex of essentially any desired stability by adjusting the base composition and/or length of the complementary PA sequences. In certain aspects, if necessary, the PA sequence duplex can be made more stable than the probe:primer-extension product duplex. The PA primer sequence may incorporate any structural modifications including duplex-stabilizing modifications like nucleotide analogs (LNA, PNA and base-modified nucleotides) and moieties like intercalators and minor groove binders, especially when these PA sequences are located at the 5'-end of the primer. In this aspect, these PA sequences can be coupled to the 5'-end through an "extendable" or "non-extendable" (or polymerase deficient) linkers of any kind. In respect to each of the complementary PA sequences of the primer and probe, the PA sequences can incorporate structural modifications which enhance the stability of the PA duplex through hydrophobic, stacking, ionic, hydrogen bond (other than complementary nucleotide interaction), covalent bond, or a combination thereof. In certain methods of the invention, the PA primer and probe sequences can benefit incorporating well-known isoguanosine and isocytosine nucleosides as well as other "non-standard" base modifications according to teaching of Benner S. A., 2000. The use of these modifications may prevent binding of the corresponding anchoring sequences anywhere else but to each other.

Figure 2:
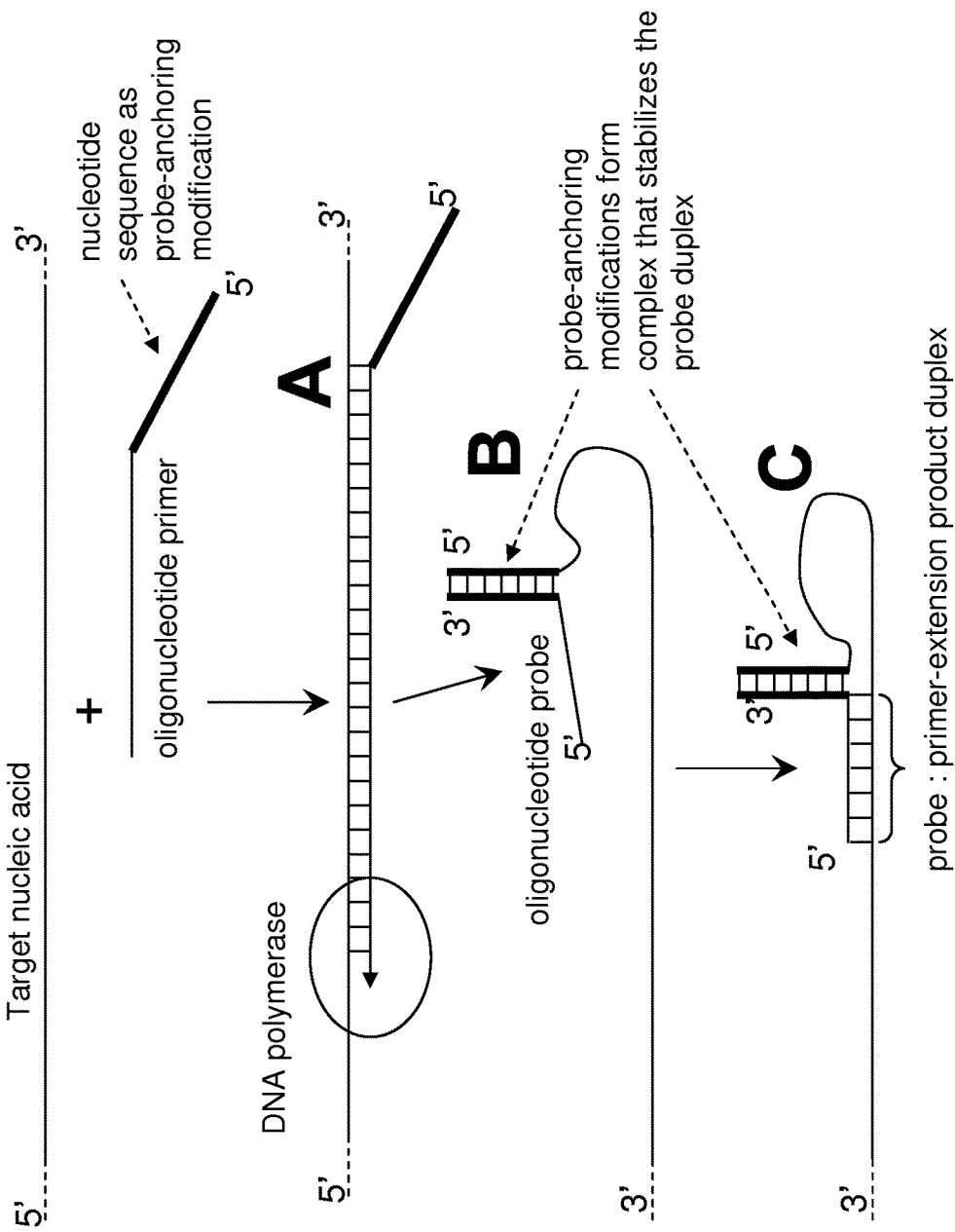
FIG. 2 shows, according to particular exemplary aspects of the present invention, a mechanism of detection of a target nucleic acid, wherein a PA modification of an oligonucleotide primer comprises a nucleotide sequence and this PA sequence is not complementary to the target nucleic acid or products of its amplification and located at the 5'-end of the primer. The primer hybridization followed by DNA polymerase extension leads to synthesis of a double-stranded primer-extension product (stage A) which is then rendered single-stranded. An oligonucleotide probe comprises a PA sequence that is located at the 3'-end of the probe and complementary to the PA sequence incorporated to the 5'-end of the primer-extension product. Under suitable reaction conditions, the PA sequences of the probe and the primer-extension product hybridizes to each other to form a complementary complex (stage B). Once the complex is formed, hybridization of the probe to the primer-extension product (stage C) becomes an intramolecular reaction, and this stabilizes the probe:primer-extension product duplex.
Figure 3:
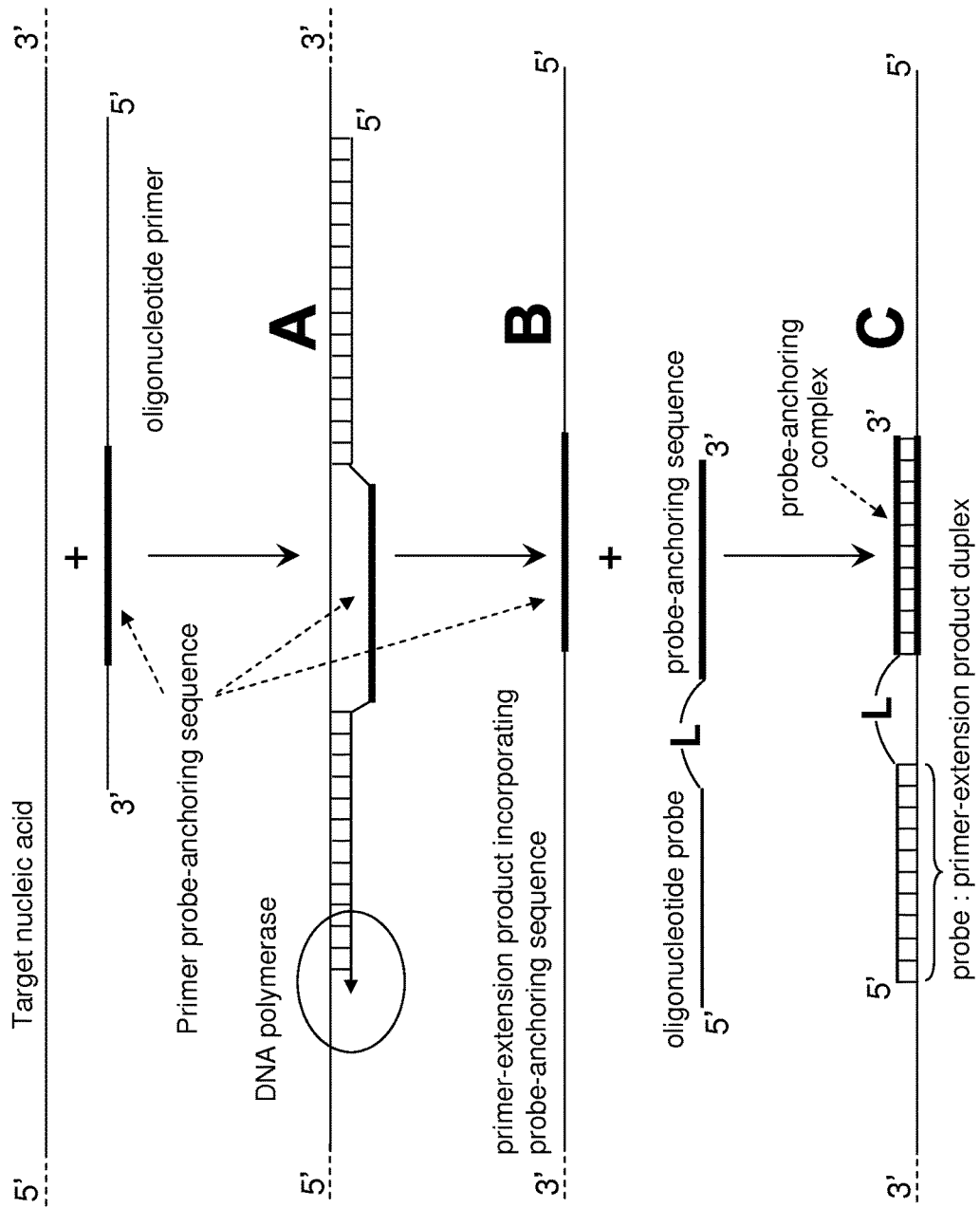
FIG. 3 illustrates particular exemplary aspects of the present invention wherein a PA modification of an oligonucleotide primer comprises a nucleotide sequence and this PA sequence (shown by thick black line) is not complementary to the target nucleic acid or products of its amplification and located within the primer sequence, preferably closer to the 3'-end. The primer hybridization to a target nucleic acid followed by DNA polymerase extension leads to synthesis of a double-stranded primer-extension product (stage A) which is then rendered single-stranded (stage B). An oligonucleotide probe comprises a PA sequence that is located at the 3'-end of the probe and complementary to the corresponding PA sequence incorporated to the primer-extension product. L is a linker that couples the 3'-end of the probe to the 5'-end of the PA probe sequence. The linker can be of any composition and length. In certain aspects, the linker is absent wherein the probe and PA sequences represent continuous chain of nucleotides. Under suitable reaction conditions, the PA sequences of the probe and the primer-extension product hybridizes to each other to form a complementary complex (stage C), and this correspondingly stabilizes the probe:primer-extension product duplex resulting in detection of the target nucleic acid.

FIGS. 2 and 3 illustrate, respectively, incorporation of the PA sequences at or near the 5'-end of the primer-extension product. According to the mechanism shown in FIG. 6, the PA sequences can be introduced at or near the 3'-end of the primer-extension product. In this aspect, the structural modification of the PA sequences is preferably limited to use of natural nucleotides and certain modified nucleotides that can be incorporated by DNA polymerase during the primer-extension applying the respectively modified nucleoside 5'-triphosphates as for example described in Kutyavin I. V. (2007b). Preferred locations of the PA sequences within the probes are the probe ends. The end preference depends on particular methods of the invention. For example, the PA sequence is preferably located at the 3'-end of the probe in methods of FIG. 2 whereas, in methods of FIG. 6, the preferred location is the 5'-end.

Methods of the invention can be used to detect more than one, a plurality of the target nucleic acids in a multiplex detection format. The term "multiplexed detection" refers to a detection reaction wherein multiple or plurality of target nucleic acids are simultaneously detected. "Multiplexed amplification" correspondingly refers to an amplification reaction wherein multiple target nucleic acids are simultaneously amplified. In methods of multiplex detection, a plurality of complementary oligonucleotide primers in each case having at least one probe-anchoring primer modifications and a respective plurality of oligonucleotide probes in each case comprising at least one probe-anchoring probe modification are provided to detect a corresponding plurality of target nucleic acid sequences.

In preferred aspects, the oligonucleotide primer which incorporates a PA modification further comprises a "probe-directing sequence" or "PD sequence" which, unlike the PA sequences, is designed complementary to the primer-extension product and which, under the detection reaction conditions, provides for primer-extension product to fold into a stem-loop structure and wherein the stem of the structure is formed between the probe:primer-extension product duplex and the primer sequence or its complement incorporated into primer-extension product. The term "secondary structure" refers to an intermolecular duplex formation of one sequence in a polynucleotide with another sequence in the same polynucleotide due to complete or partial complementarity between these two sequences. The terms "hairpin" structure or "stem-loop" structure are also used herein describing elements of secondary structure and both terms refer to a double-helical region (stem) formed by base pairing between complementary sequences in a single strand RNA or DNA.

Figure 4:
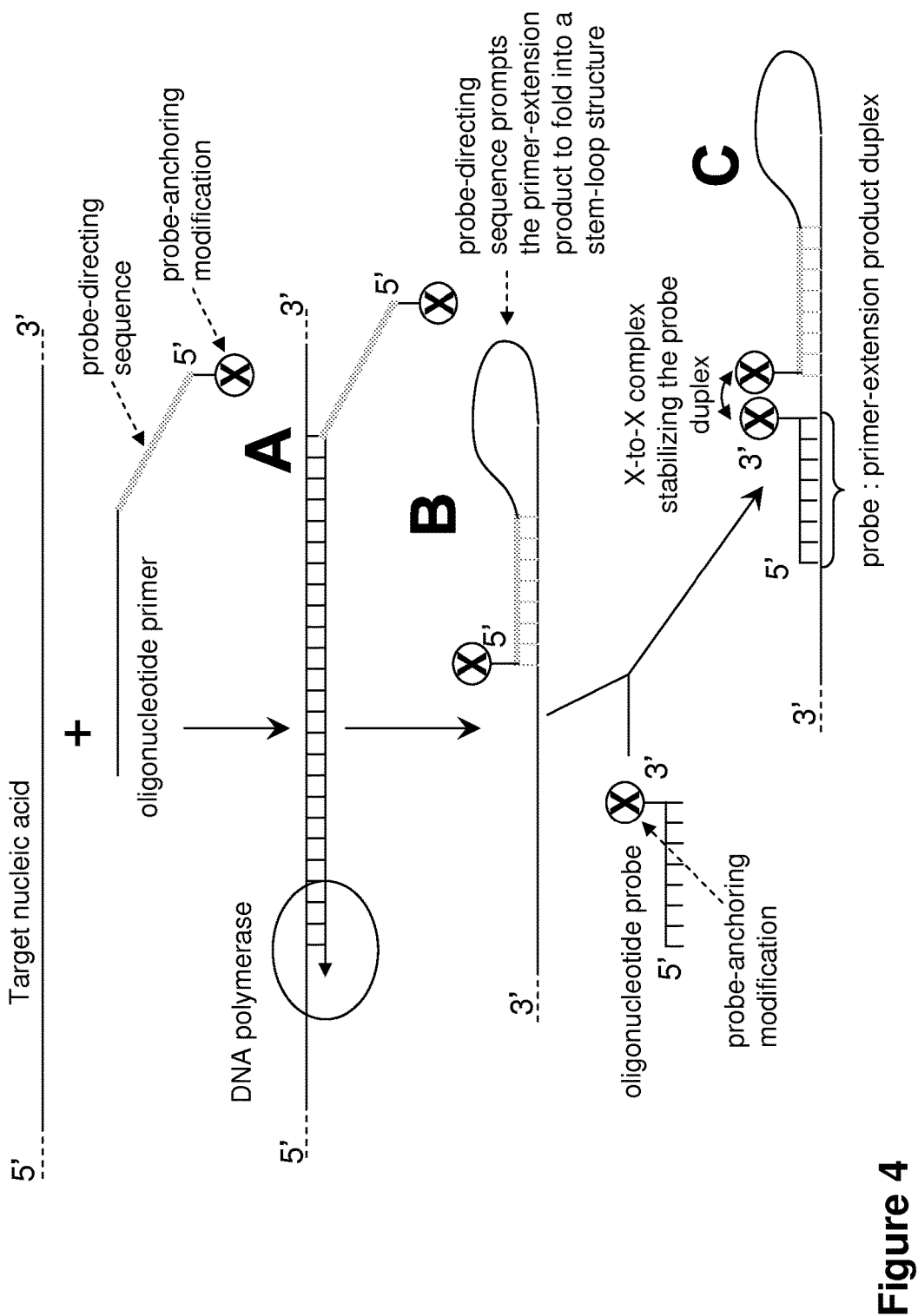
FIG. 4 illustrates particular exemplary aspects of the present invention in detecting target nucleic acids. In these exemplary methods, an oligonucleotide primer, in addition to a PA modification, comprises a probe-directing (PD) nucleotide sequence (shown by thick gray line) at the 5'-end of the primer. The primer hybridization to a target nucleic acid followed by DNA polymerase extension leads to synthesis of a double-stranded primer-extension product (stage A) which is then rendered single-stranded. Consequently, this provides for a single-stranded primer-extension product carrying the PA modification and PD sequence at its 5'-end. In the shown example, the PD sequence is not complementary to the detected target nucleic acid, but it is designed to form a duplex with the product of the primer extension. Under suitable reaction conditions, this induces the single-stranded primer-extension product to fold into a stem-loop structure (stage B). An oligonucleotide probe comprising a respective PA modification at the 3'-end is designed to hybridize to the primer-extension product such as the probe:primer-extension duplex is formed next to or nearby the stem of the structure. This brings into proximity the corresponding PA modifications of the probe and primer-extension product, provides for the PA modifications to interact with each other and results in stabilization of the probe:primer-extension product duplex.
Figure 5:
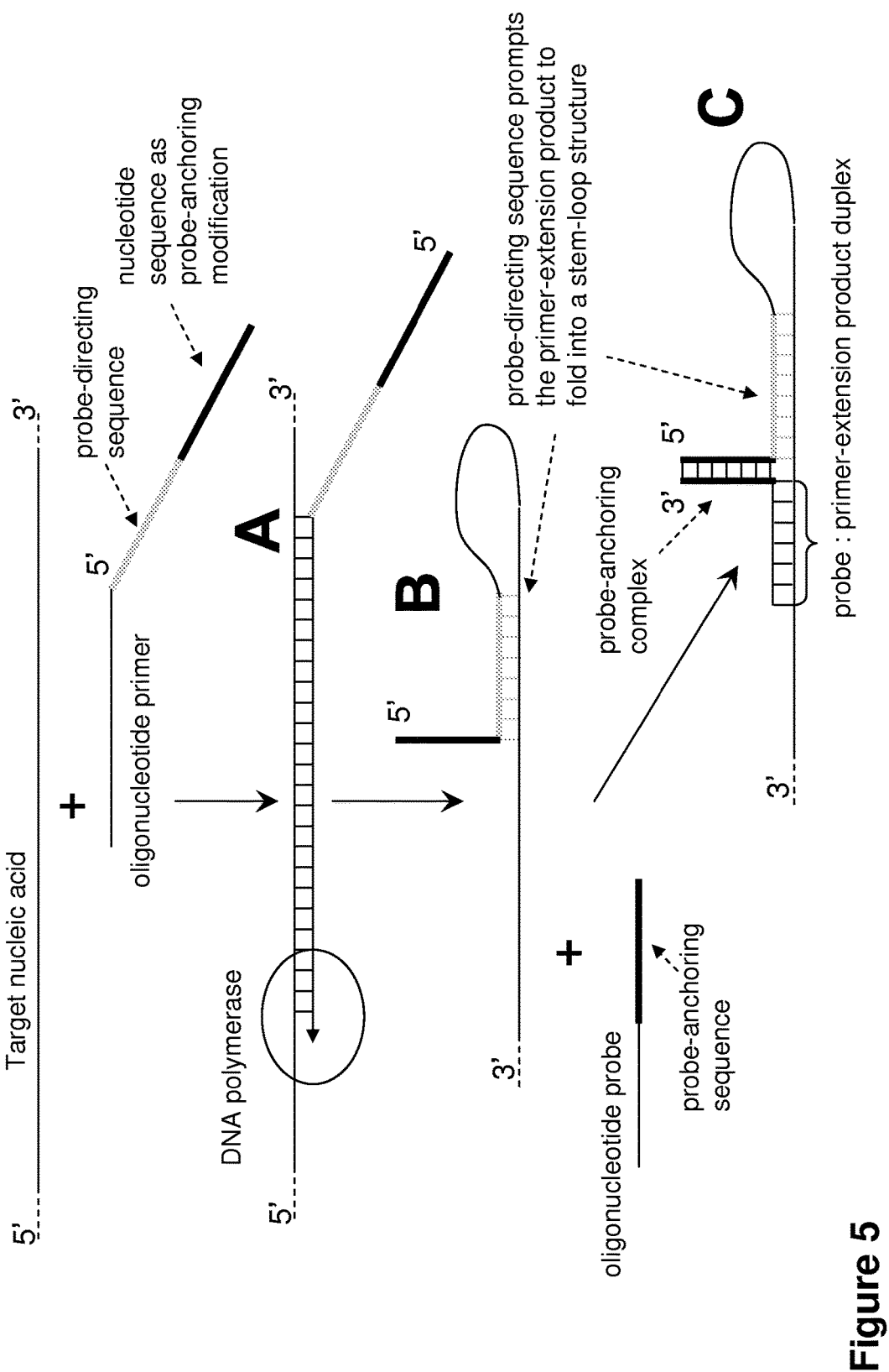
FIG. 5 shows particular exemplary aspects of the detection methods illustrated in FIG. 4. In these exemplary methods, a PA modification (shown by thick black line) comprises a nucleotide sequence followed in 5'→3' direction by a probe-directing (shown by thick gray line) and oligonucleotide primer sequences. In particular, the diagram shows that use of this primer and a corresponding oligonucleotide probe leads to formation of a three-way DNA junction (stage C) wherein one of the junction duplexes is provided by a primer-extension product which folds into a secondary structure. The three-way DNA junction formation stabilizes the probe:primer-extension product duplex and provides for the nucleic acid detection.
Figure 6:
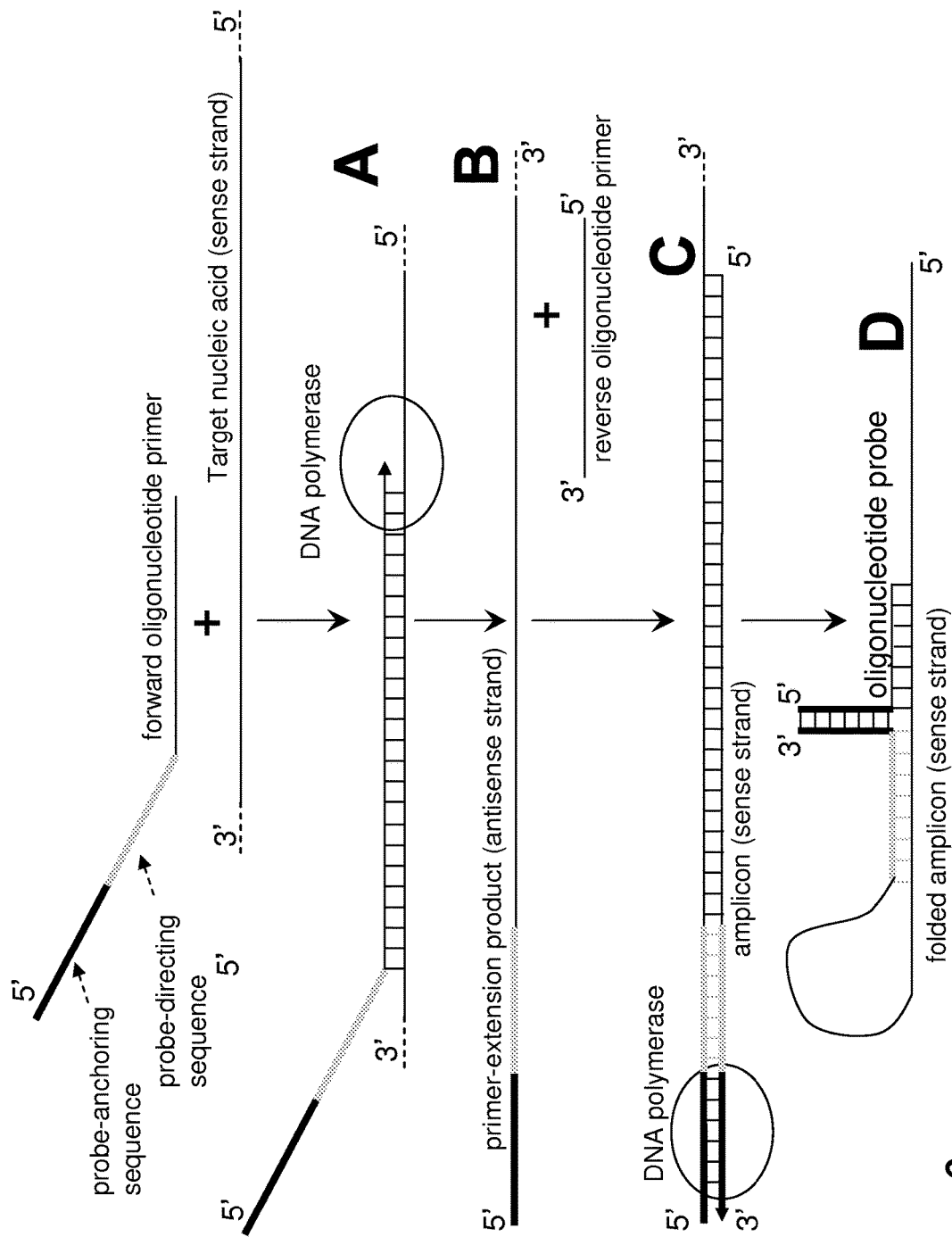
FIG. 6 further illustrates particular aspects of the detection methods shown in FIG. 5. In the methods of FIG. 5, the 5'-end of the primer-extension product folds into a stem-loop structure. Alternatively, FIG. 6 exemplifies stages of a mechanism to produce amplicons which also fold into a secondary structure but at the 3'-end. Similar to the methods of FIG. 5, an oligonucleotide probe incorporates a PA sequence, but at the 5'-end of the probe. Respectively, hybridization of the probe to the folded amplicon (stage D) results in a three-way DNA junction formation and stabilization of the duplex between the probe and primer-extension product. The methods of FIG. 6 are, in particular, useful when target nucleic acids are amplified.
Figure 7:
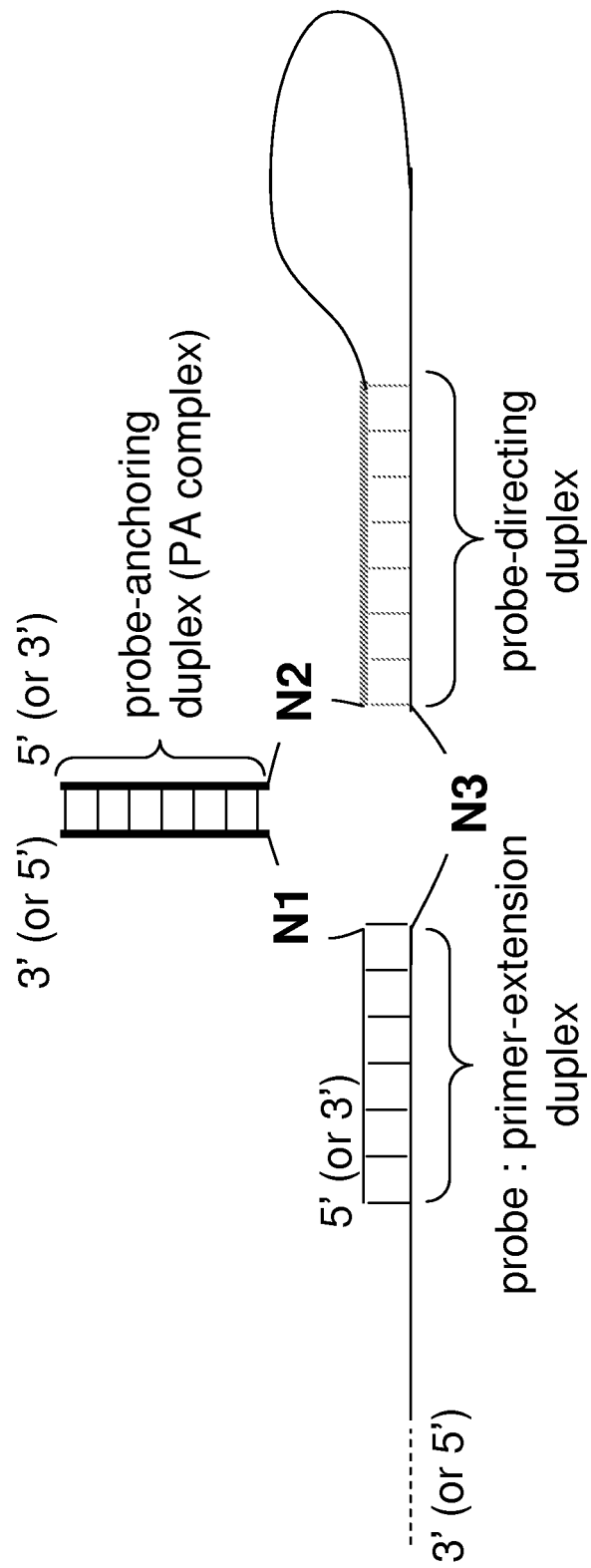
FIG. 7 shows an exemplary schematic diagram of three-way DNA junction that is formed in particular preferred methods of the invention to enhance hybridization properties of oligonucleotide probes in complementary binding to the detected nucleic acids. Depending on the particular methods shown in FIG. 5 or 6, the assignment of sequence ends (5' or 3') changes as indicated. One of the three duplexes, in particular, the probe-directing duplex is provided by amplification product folded into secondary structure. N1, N2 and N3 are linkers. N1 linker can be of any composition (e.g. nucleotide sequence or unnatural chemical linker). The same applies to the linker N2 when methods of FIG. 5 are used. In case of the methods of FIG. 6, N2 linker comprises nucleotide sequences. The N3 linker can only comprise nucleotide sequences regardless of the detection methods used. The linkers may be of any suitable length. In preferred embodiments, the linkers are absent or short providing a length that is equivalent to mono-, di-, or trinucleotide sequence.

As illustrated in FIG. 4, the PD sequence helps to deliver a PA modification of a primer in close proximity to a corresponding PA modification of a probe hybridized to a primer-extension product. This PA modification delivery, in turn, stabilizes the PA modification complex and consequently results in stabilization of the probe:primer-extension product duplex. In preferred embodiments, the PA modification comprises a nucleotide sequence. Examples of these methods of the invention are illustrated in FIGS. 5 and 6. In preferred aspects, an oligonucleotide primer incorporates a PA sequence at the 5'-end followed by a PD sequence and then by a sequence of the primer. This primer design, in particular, allows formation of a "three-way DNA junction"; a molecular structure that, as shown in the instant working examples provided herein, can significantly stabilize the probe:primer-extension product duplex and may be especially useful in applications involving the use of exceptionally short oligonucleotide probes. PD sequences in methods of FIG. 5 may incorporate structural modifications of any kind. In this aspect, the rules for use of the structural modifications in the PD sequences are similar to those discussed for the PA sequences. In contrast to the methods of FIG. 5, the structural modifications of the PA sequences used in the methods of FIG. 6 are limited to natural nucleotides and certain modified nucleotides that can be incorporated by DNA polymerase during the primer-extension. Other aspects, related to use of structural modification in design of primers comprising PA and PD sequences are discussed in FIG. 7.

In exemplary methods of the invention, formation of the probe:primer-extension product duplex can be detected by any appropriate physical, chemical or biochemical approach. In preferred embodiments, the oligonucleotide probe comprises a detectable label. The term "label" refers to any atom or molecule that can be used to provide a detectable signal and that can be attached to a nucleic acid or oligonucleotide. Labels include but are not limited to isotopes, radiolabels such as $^{32}P$, binding moieties such as biotin, haptens, mass tags, phosphorescent or fluorescent moieties, fluorescent dyes alone or in combination with other dyes or moieties that can suppress or shift emission spectra by FRET effect. Labels may provide signals detectable by fluorescence, radioactivity, colorimetry, gravimetry, X-ray diffraction or absorption, magnetism, enzymatic activity, mass spectrometry, binding affinity and the like. A label may be a charged moiety or alternatively, may be charge neutral. Labels can include or consist of nucleic acid or protein sequence, so long as the sequence comprising the label is detectable. In preferred embodiments, the label is fluorescent label. "Fluorescent label" refers to a label that provides a fluorescent signal. A fluorescent label is commonly a fluorescent dye, but it may be any molecule including but not limited to a macromolecule like a protein, or a particle made from inorganic material like quantum dots, as described, for example, in (Robelek R. et al, 2004).

In particular preferred embodiments, the probes of the invention are FRET probes and the detection of target nucleic acids is based on FRET effect. "FRET" is an abbreviation of Förster Resonance Energy Transfer effect. FRET is a distance-dependent interaction occurring between two dye molecules in which excitation is transferred from a donor to an acceptor fluorophore through dipole-dipole interaction without the emission of a photon. As a result, the donor molecule fluorescence is quenched, and the acceptor molecule becomes excited. The efficiency of FRET depends on spectral properties, relative orientation and distance between the donor and acceptor chromophores (Förster T., 1965). As used herein, "FRET probe" refers to a fluorescent oligonucleotide that is used for detection of a nucleic acid of interest, wherein detection is based on FRET effect. The acceptor chromophore may be a non-fluorescent dye chosen to quench fluorescence of the reporting fluorophore (Eftink M. R., 1991). Formation of sequence-specific hybrids between the target nucleic acid and the probes leads to changes in fluorescent properties of the probe providing for detection of the nucleic acid target. FRET is widely used in biomedical research and particularly in probe designs for nucleic acid detection (e.g., in Didenko V. V., 2001).

Many detection strategies and designs exploiting the FRET effect are known in the art, and these strategies may be used in design of the FRET probes of the invention. In particular aspects, the FRET probes are hybridization-triggered FRET probes. The "hybridization-triggered FRET probe" approach is based on distance change between the donor and acceptor dyes as result of a sequence specific duplex formation between a target nucleic acid and a fluorescent oligonucleotide probe. For example, the probes of the methods of FIGS. 1-6 can be labeled by two FRET dyes conjugated to the opposite ends of the probe sequences. When the probes are unhybridized, the quencher moiety is sufficiently close to the reporter dye to quench its fluorescence due to random oligonucleotide coiling. Once the probes are hybridized to the primer-extension products forming, according to the methods of FIGS. 1-6, rigid duplex or tree-way DNA junction structures, the quencher and reporter moieties are separated, thus enabling the reporter dye to fluoresce and providing for the target nucleic acid detection (e.g., Livak K. J. et al, 1998). Examples of other hybridization-triggered FRET system designs that can be used practicing the present invention include but not limited to "Adjacent Hybridization Probe" method (e.g. Eftink M. R., 1991; Heller M. J. and Morrison L. E., 1985), "Molecular Beacons" (Lizardi P. M. et al, 1992), "Eclipse Probes" (Afonina I. A. et al, 2002), all of which are incorporated herein by the reference.

In particular preferred aspects, the methods of the invention further comprise a nuclease, wherein the nuclease recognizes the probe duplex with the target primer-extension product or amplification product and cleaves the probe providing cleavage products, wherein detecting comprises detecting of at least one of the cleavage products, and wherein the presence of the cleavage product is indicative of the presence of the target nucleic acid sequence in the test sample. As used herein, the term "nuclease" refers to an enzyme which expresses a phosphomonoesterase or phosphodiesterase activity and capable of cleaving a phosphorester bond in compounds such as R'—O—P(O)(OH)$_2$ and R'—O—P(O)(OH)—O—R" resulting in products R'—OH+ P(O)(OH)$_3$ and R'—OH+P(O)(OH)$_2$—O—R" (or R"—OH+ P(O)(OH)$_2$—O—R'), respectively, and wherein R' and R" may be moieties of any structure which are not necessarily of a nucleotide nature. The term "nuclease" incorporates both "exonuclease" and "endonuclease."

Figure 8:
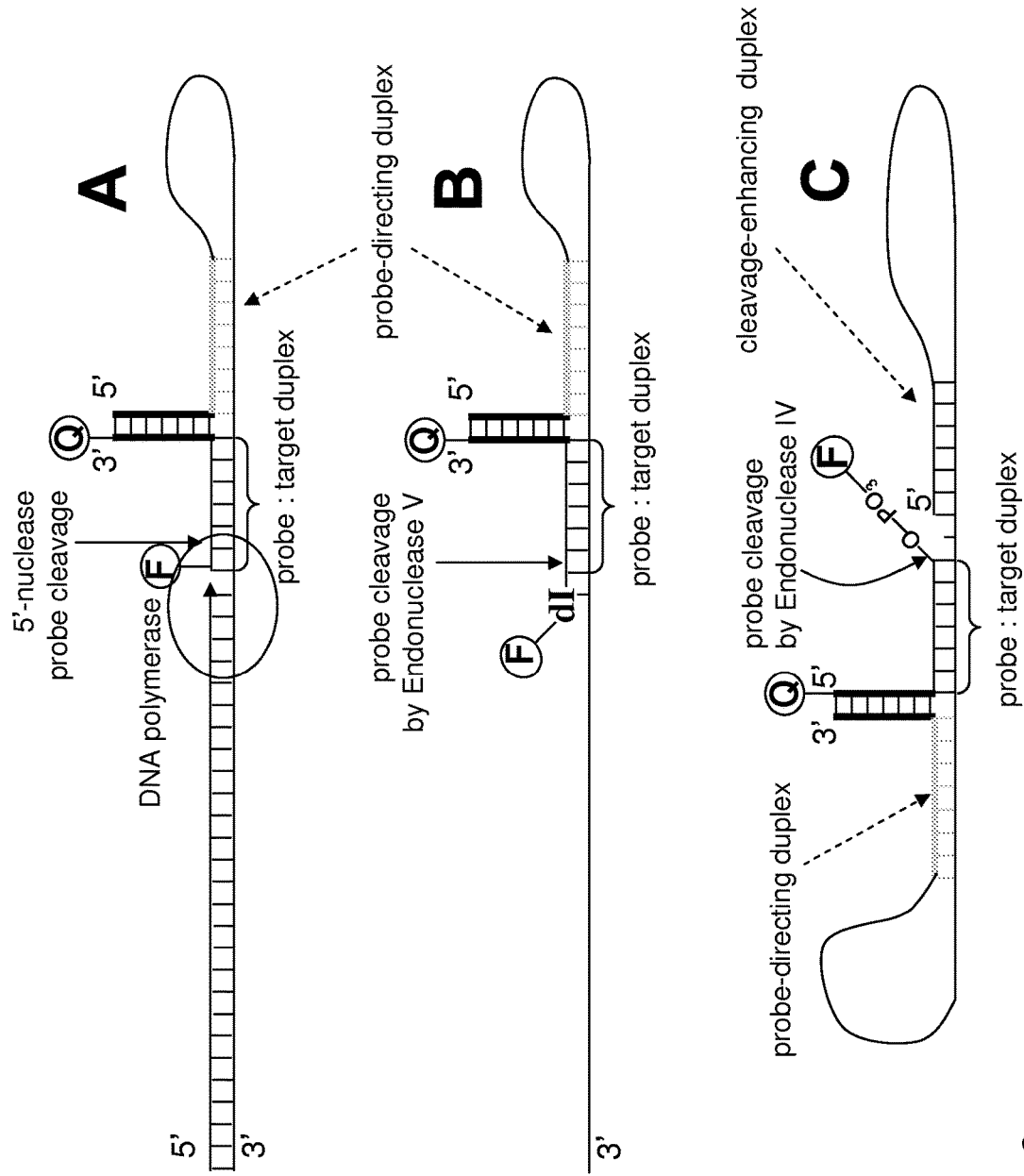
FIG. 8 illustrates particular exemplary aspects of the invention wherein detection of nucleic acids is based on FRET effect and provided by cleavable oligonucleotide probes. In all shown examples the probe stabilization is achieved through formation of the three-way DNA junctions (see structure in FIG. 7) that can be obtained according to methods of FIGS. 5 and 6.

In certain aspects, detection of nucleic acids using nuclease-cleavable probes (e.g., Duck P. et al, 1989) provides an advantage over the methods based on direct detection of the probe:target duplex. The FRET-based detection is an example. In contrast to the hybridization-triggered FRET approaches, the FRET methods employing nuclease-cleavable FRET probes commonly result in better detection signal improving the assay sensitivity because, when the probe cleavage takes place somewhere between the conjugated FRET dyes, this permanently and irreversibly disrupts FRET. Selection of an appropriate cleavable-probe technology for use in the methods of the invention is based on two main provisions. First, the cleavage reaction has to be duplex-specific so the probe gets cleaved when it is hybridized to the target. Second, the nuclease needs to recognize and preferentially cleave the probe strand in the probe:target duplex. Examples of the probe-cleavable technologies which may be used in methods of the invention include but not limited to Taqman™ technology (5'-nuclease assays, see, e.g., Gelfand D. H. et al, 1993 and 1996); chimeric DNA-RNA probes that are cleaved by RNAse H upon the binding to target DNA (see, e.g. Duck P. et al, 1989); INVADER™ assay that utilizes the "flap" or 5'-endonuclease activity of certain polymerases to cleave two partially overlapping oligonucleotides upon their binding to target DNA (see, e.g., Dahlberg, J. E. et al, 1995, 1997 and 1998); target-specific probe cleavage based on the substrate specificity of Endonuclease IV (Kutyavin I. V. et al, 2007) and Endonuclease V from E. coli. Use of these detection techniques in methods of the invention is illustrated in FIG. 8.

Preferably, oligonucleotide probes are cleaved by nucleases only when they hybridized to target nucleic acids. In regard to art-recognized detection methods that are based on probe cleavage, this is not always possible to achieve, and the oligonucleotide probes are commonly cleaved in the absence of the target nucleic acids, although usually at lower rates than in the presence of the nucleic acids of interest. To some extent, the probes' cleavage in the absence of the target nucleic acids may also occur in certain methods of the invention. Particular techniques have been established in the art to avoid false-positive detection in such cases and these approaches are described, e.g. in Duck P. et al, 1989; Fong W. et al, 2000; Harvey J. J. et al, 2004; Gelfand D. H. et al, 1993 and 1996; Dahlberg, J. E. et al, 1997 and 1998; Kutyavin I. V. et al, 2006 and 2007, and in many other similar manuscripts which are incorporated herein by reference. For example, a "control" reaction can be performed that is otherwise identical to the detection reaction but that does not incorporate the test sample (no-target control). If amount of cleavage products in the detection reaction exceeds the same in the control reaction, this indicates the presence of the target nucleic acid sequence in the test sample whereas equal amounts of the cleavage products in both reactions indicates the absence of the target nucleic acid sequence in the test sample. The control reactions can be also performed with known and variable amounts of the target nucleic acid and the comparison of these control reactions with the detection reaction in a test sample can be used in methods of the invention for determining the amount of the target nucleic acid in or from the sample. Preferably, the terms "detecting," "detecting a target" and "detecting a cleavage product" incorporate performing the discussed control reactions, or correlation with a contemporaneous or historical control values. Performing the control reactions is particularly useful when the methods of the invention are used for measuring of amounts of target nucleic acids in samples and this applies to all methods of the invention including the hybridization-triggered and cleavable probe detections. In a particular aspect, the methods of the invention can be used for determining amount of the target nucleic acid in or from the sample. In another particular aspect, the methods can be used for detecting polymorphic variations of a target nucleic acid. As shown in the instant working examples provided herein, the polymorphic variation can be as small as single nucleotide polymorphism. In these methods, the homologous target nucleic acids can be amplified and the primer-extension product can be produced using the same set of the primers or the same primer, respectively. In these cases, however, a corresponding PA probe is provided for each target or target polymorphic variation to be detected.

In preferred aspects of the invention, the cleavage of the probe is performed in a cycling mode. As used herein, the term "cycling mode" refers to a probe-cleavage process wherein more than one probe can be cleaved per a target molecule sequence. This usually occurs when a hybridized probe is cleaved internally, the cleavage products form weaker hybrids than the original, intact probe and dissociate from the target strand, leaving that strand available for additional rounds of the cleavage reaction (e.g., target cycling, or probe cycling at a target sequence). Additional information for performing the probe cleavage reaction in a cycling mode can be found, e.g., in U.S. Pat. Nos. 5,011,769 and 5,403,711 (Duck P., Bender R., 1991; Walder J. A., Walder R. Y., 1995), all of which are incorporated herein by the reference for their relevant teachings.

Amounts of target nucleic acids in samples are commonly limited for the direct detection. In particular embodiments, a target sequence is amplified to provide target amplicons incorporating a probe-anchoring primer modification and the target detection is provided by detecting a duplex of an oligonucleotide probe comprising a probe-anchoring probe modification hybridized to a target amplicons. In other preferred embodiments, the target amplification products incorporating PA modification are amplified by one of PCR and an isothermal reaction. In particular aspects, "amplification" and "amplifying" target nucleic acids, in general, refers to a procedure wherein multiple copies of the nucleic acid of interest are generated in the form of DNA copies. The terms "amplicon" or "amplification product" refer to a primer-extension product or products of amplification that may be a population of polynucleotides, single- or double-stranded, that are replicated from either strand or from one or more nucleic acids of interest. Regardless of the originating target nucleic acid strand and the amplicons state, e.g. double- or single-stranded, all amplicons which are usually homologous are treated herein as amplification products of the same target nucleic acid including the products of incomplete extension. In particular aspects, the term "homology" and "homologous" refers to a degree of identity between nucleic acids. There may be partial homology or complete homology.

In certain aspects, the amplification and detection stages of the invention may be performed separately when the detection stage follows the amplification. The terms "detection performed after the amplification," "target nucleic acid is amplified before the detection reaction" and "post-amplification detection" are used herein to describe such assays. In preferred embodiments of the present invention, detection of the target nucleic acids can be performed in "real-time." Real-time detection is possible when all detection components are available during the amplification and the reaction conditions such as temperature, buffering agents to maintain pH at a selected level, salts, co-factors, scavengers, and the like support both stages of the reaction, amplification and the detection. This permits a target nucleic acid to be measured as the amplification reaction progresses, decreasing the number of subsequent handling steps required for the detection of amplified material. "Real-time detection" means an amplification reaction for which the amount of reaction product, i.e. target nucleic acid, is monitored as the reaction proceeds. Reviews of the detection chemistries for real-time amplification can be also found in Didenko V. V., 2001, Mackay I. M. et al, 2002, and Mackay J., Landt O., 2007, which are incorporated herein by reference for their relevant teachings. In preferred embodiments of the present invention, real-time detection of nucleic acids is based on use of FRET effect and FRET probes.

In particular aspects, "isothermal amplification" and "isothermal amplification reaction" refers to a process which generates multiple copies of a target nucleic acid, and which, unlike PCR, does not require temperature changes during the amplification (temperature cycling), and which may rather be conducted at a relatively constant temperature. Reaction temperature in isothermal amplification, including in methods of the invention may fluctuate somewhat, but is not required for the purpose of amplicon strand separation as in PCR. A number of art-recognized isothermal amplification techniques may be used in methods of the invention to produce target amplification product incorporating probe-anchoring modifications, e.g. according to the mechanisms illustrated in FIGS. 1-6. Examples of these amplification technologies include but are not limited to NASBA (e.g., Davey C. and Malek L. T., 2000; Oehlenschlager F. et al, 1996), HDA (e.g., Vincent M. et al, 2004; An L. et al., 2005), Rolling Circle Amplification (Lizardi P., 1998 and 2001), Loop-mediated isothermal amplification (Notomi T. and Hase T., 2002), all of which are incorporated herein by reference for their relevant teachings.

Certain amplification protocols are based on DNA strand displacement and repeated cleavage of the primer-extension products at or nearby a nick-directing modification or sequence to generate new priming site for DNA polymerase. Examples of these amplification schemes include amplification methods based on the use of RNA or composite RNA/DNA primers (e.g., Cleuziat P. and Mandrand B., 1998; Kurn N., 2001; Sagawa H. et al, 2003), Strand Displacement Amplification (e.g., Walker G. T. et al, 1993; Walker G. T. et al, 1996; Fraiser M. S. et al, 1997; Walker G. T., 1998), Nick Displacement Amplification (Millar D. S. et al, 2006; Van Ness J. et al, 2003a and 2003b), Accelerated Cascade Amplification (Nelson J. R. et al, 2008; Kutyavin I., 2009), all of which are incorporated herein by reference for their relevant teachings. In particular aspects of these amplification methods, the 5'-end portion of primers may not be incorporated into the primer-extension product. In these cases, the PA modifications as well as PD sequence may be incorporated into the primer-extension product by placing the respective PA modification and, when it applies, the PD sequence between the nick-directing modification and the 3'-end of the primer according, for example, to the method shown in FIG. 3. This design presumes, however, that the incorporation of the PA modification and, in certain aspects, PD sequence does not block the primer capability to be extended by a DNA polymerase when the primer is hybridized to a target nucleic acid or amplification product thereof. The term "nick-directing modification" or "nicking modification" has very broad meaning and refers to any approach or structural entity (modification) or combination thereof within double-stranded oligonucleotides or polynucleotides, which direct a nuclease to cleave preferentially that one, of the two duplexed strands, which incorporates the nicking modification. For example, deoxyinosine can be used as a nicking modification in design of the probes that are cleaved in the presence of Endonuclease V when the probe is hybridized to a primer-extension product as illustrated in FIG. 8B.

In a particular preferred embodiment of the invention, a target nucleic acid is amplified by PCR providing target amplicons comprising a PA modification. "PCR" is an abbreviation of term "polymerase chain reaction," the art-recognized nucleic acid amplification technology (e.g., U.S. Pat. Nos. 4,683,195 and 4,683,202 to Mullis K. B.). The commonly used PCR protocol employs two oligonucleotide primers, one for each strand, designed such that extension of one primer provides a template for the other primer in the next PCR cycle. Generally, a PCR reaction consists of repetitions (or cycles) of (i) a denaturation step which separates the strands of a double-stranded nucleic acid, followed by (ii) an annealing step, which allows primers to anneal to positions flanking a sequence of interest, and then (iii) an extension step which extends the primers in a 5' to 3' direction, thereby forming a nucleic acid fragment complementary to the target sequence. Each of the above steps may be conducted at a different temperature using an automated thermocycler. The PCR cycles can be repeated as often as desired resulting in an exponential accumulation of a target DNA amplicon fragment whose termini are usually defined by the 5'-ends of the primers used. Particular temperatures, incubation times at each step and rates of change between steps depend on many factors well-known to those of ordinary skill in the art and the examples can be found in numerous published protocols (e.g., McPherson M. J. et al., 1991 and 1995). Although conditions of PCR can vary in a broad range, a double-stranded target nucleic acid is usually denatured at a temperature of >90° C., primers are annealed at a temperature in the range of about 50-75° C., and the extension is preferably performed in the 72° C.-80° C. range. The term "PCR" encompasses derivative forms of the reaction, including but not limited to, "RT-PCR," "real-time PCR," "asymmetric PCR," "nested PCR," "quantitative PCR," "multiplexed PCR," and the like.

When target nucleic acids are amplified by PCR in methods of the invention, at least two primers are provided for every target nucleic acid to be amplified and detected wherein at least one of the primers comprises a PA modification to produce target amplicons incorporating the PA modification. In particular embodiments, the primer that comprises at least one probe-anchoring primer modification further comprises at least one probe-directing sequence. In preferred embodiments, the probe-anchoring modification comprises a nucleotide sequence. The PA and PD sequences can incorporate any kind of structural modification including but not limited to, in particular, the duplex-stabilizing modifications. In preferred aspects, the PCR-based detection methods comprise a 5'-nuclease wherein the 5'-nuclease recognizes the probe:target amplification product duplex and cleaves the probe as this is illustrated in FIG. 8A. A DNA polymerase originated from *Thermus aquaticus* was used in instant working examples provided herein (Jump-Start™ Taq DNA polymerase from Sigma). The enzyme utilizes the 5'-3' exonuclease activity and cleaves the FRET-labeled probes. Alternatively, the DNA polymerase can have no 5'-nuclease activity and this enzymatic activity can be supplied by a 5'-flap endonuclease. "Flap endonucleases" are yet another example of 5'-duplex-specific nucleases that may be used to cleave the optimal cleavage structures shown in FIGS. 8A and 9F. Flap endonucleases are a class of nucleolytic enzymes that act as structure-specific 5'-exo and 5'-endonucleases during DNA replication, DNA repair and DNA recombination (Lyamichev V. et al, 1993). Flap endo-nucleases have been identified in eukaryotes, prokaryotes, archea and viruses. Preferred 5'-nucleases of the invention are thermophilic. However, mesophilic 5'-endonucleases may be used in certain post-amplification assays of the invention. In other preferred methods of the invention that are based on PCR and 5'-nuclease cleavable probes, the Taq DNA polymerase activity is supplemented by 5'-flap endonuclease activity.

Figure 9:
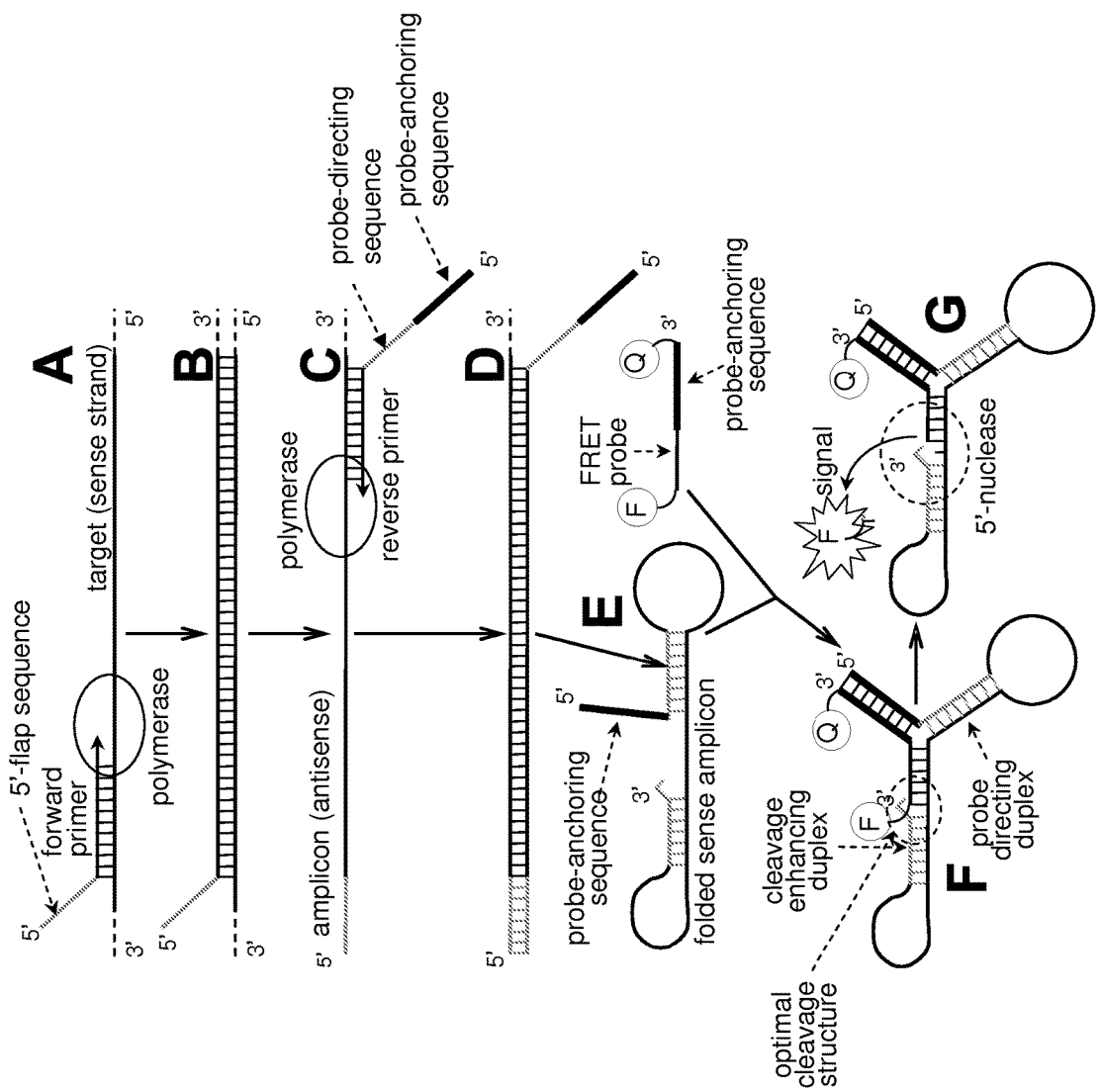
FIG. 9 shows a mechanism of signal generation in one of the preferred exemplary embodiments of the invention, wherein a target nucleic acid is amplified by PCR and detection in performed in real time using 5'-nuclease cleavable FRET probes. A forward primer contains a 5'-flap sequence (shown in gray) which is complementary, save for the 5'-terminal base, to a target site located downstream from the primer binding site. Extension of this forward primer in stage A results in the synthesis of an antisense strand, providing a double stranded amplicon (stage B). After strand separation (95° C.), a reverse primer hybridizes to the antisense strand and DNA polymerase extends the complex (stage C), resulting in yet another double stranded amplicon (stage D). The reverse primer also incorporates a 5'-flap sequence. This flap sequence comprises two sequences. The first probe-directing sequence (also shown in gray) is designed to fold the sense amplicon into a stem-loop structure. The second probe-anchoring sequence (shown in thick black) is designed to be complementary to a corresponding anchoring sequence introduced at the 3'-end of a FRET-probe (also shown in thick black). After strand separation of the double stranded amplicon produced in stage D, the sense amplicon folds into a dumbbell-like secondary structure (stage E). The probe is complementary to the target sequence of the sense amplicon located between two duplex stems (shown in gray). Hybridization of the probe to the folded sense amplicon results in the formation of a three-way DNA junction (stage F). The cleavage-enhancing duplex of the folded amplicon and the probe:target amplicon duplex form an optimal substrate for Taq 5'-nuclease, which recognizes the complex, cleaves the probe and releases a detectable fluorescence signal in stage G.
Figure 12:
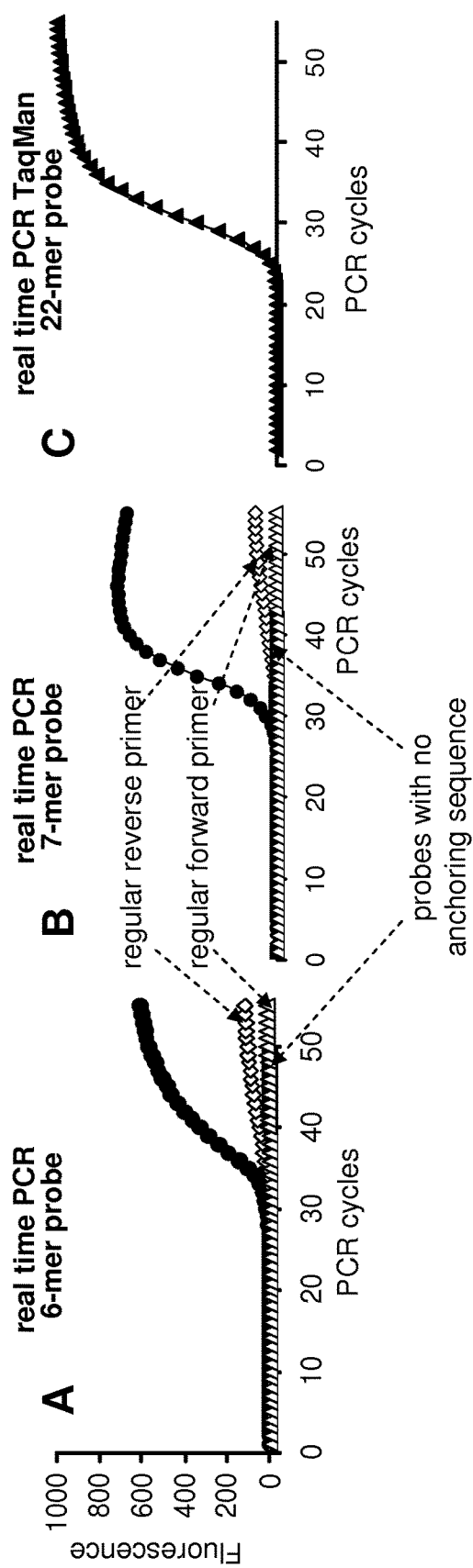
FIGS. 12 and 13 represents an average of 3-5 independent experiments.
Figure 13:
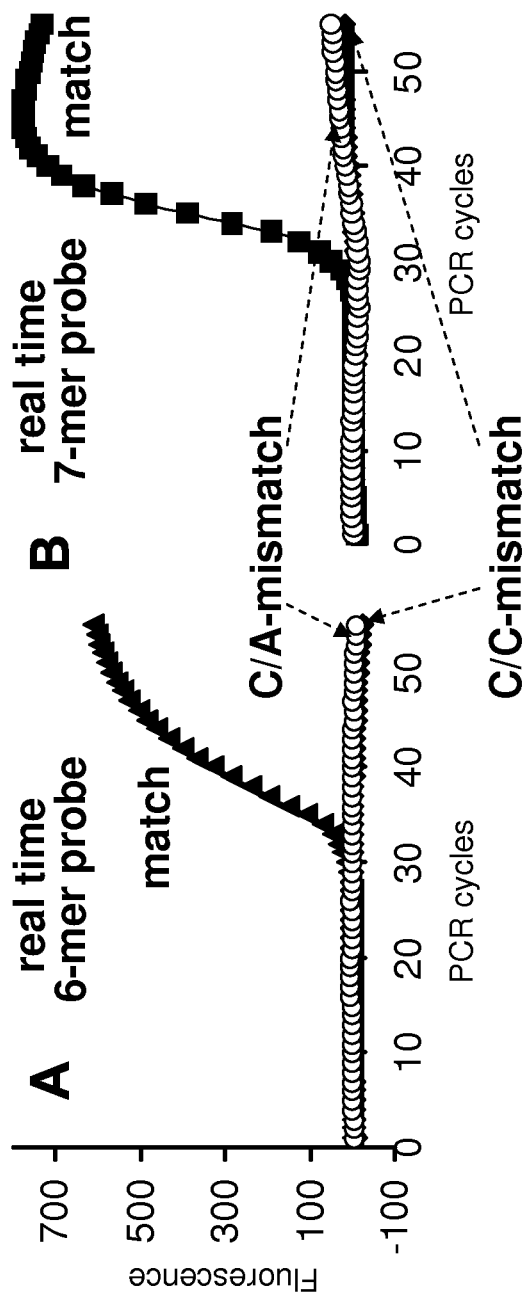

In a preferred embodiment, a/the PCR primer other than that comprising the probe-anchoring modification, further comprises a 5-flap sequence, which during the amplification provides for the target amplification products to fold into stem-loop structures and wherein, under the detection reaction conditions, one of these stem-loop structure and the probe:target amplification product duplex form an optimal cleavage substrate for 5'-nuclease. The formation of an optimal cleavage structure for 5'-nuclease provides for further enhancement of the probe cleavage process and improves the detection methods as illustrated, for example, in the instant working examples provided herein. The reaction mechanism of these exemplary methods is shown in FIG. 9. In these particular methods, a target amplicon folds into a dumbbell-like secondary structure, wherein first stem-loop structure serves to stabilize the probe:target amplicon duplex and also direct probe binding to a specific site within the target amplicon, whereas the second stem-loop structure serves to enhance the probe cleavage by forming, with the probe:target amplicon duplex an optimal cleavage structure for 5'-nuclease. The same strategy can be used in detection methods based on Endonuclease IV cleavable probes, for example, as illustrated in FIG. 8C. Detailed teachings about use of the folded target amplicons to form optimal cleavage structures with the probe:target amplicon duplex can be found in Kutyavin I. V., 2007a which is incorporated herein by the reference for such teachings. Regardless of the particular strategy in the target-specific probe cleavage, the detection reactions of the invention can be performed after the PCR amplification (e.g., FIG. 11 and working Example 2). In preferred aspects, the amplification and detection reactions are performed simultaneously, in real-time, as illustrated, for example, in FIGS. 12 and 13, and in the instant working Examples 3 and 4.

As shown in the working examples provided herein, stabilization of the probe:primer-extension product duplex, in particular, through the formation of three-way DNA junctions can be significant. This, in turn, allows substantial reduction in length of the oligonucleotide probes used for target detection compare to other conventional, art-recognized methods of probe:target duplex stabilization like base-modified (Lebedev Y. et al, 1996) and sugar-modified LNA (Wengel J., Nielsen P., 2003) and PNA (Egholm M. et al, 1993) nucleotide analogs, duplex-stabilizing tails like minor groove binders (Kutyavin I. V. et al, 1998) and intercalators (e.g., Asseline U. et al, 1984). In particular aspects, the probes used in methods of the invention comprise ten nucleotides or shorter nucleotide sequences. As used herein, the nucleotide length of the probes is determined by length of the target specific sequence and the nucleotides of the PA sequence are not counted. For instance, as shown in the Examples provided herein, the exceptionally short 6-mer and 7-mer 5'-nuclease cleavable FRET probes were capable to perform at elevated temperatures of real-time PCR (e.g., 56° C.). This does not indicate, however, that the limit in the probe length reduction has been reached. The probe sequences used in methods of the invention can be shorter than six nucleotides, up to 3-mers. This, in particular, may apply to methods of the invention based on certain isothermal amplification schemes which are performed at temperatures <50° C. and use mesophilic nucleases to cleave the probes in a target-specific fashion.

Methods of the invention can be performed in homogeneous and heterogeneous reactions. In particular heterogeneous methods of the detection, at least on of the target nucleic acid, primer, primer-extension product and probe are immobilized on solid support. The term "solid support" refers to any material that provides a solid structure with which the reaction components of the methods can be attached. Such materials may include but not limited to silicon, plastic, metal, glass, ceramic surfaces, and the like. Solid supports may be of a rigid or non-rigid nature like gels, rubbers, polymers, etc. and may be any type of shape including spherical shapes like beads. A reaction component is "immobilized" to a solid support when it is associated with the solid support through a random or non-random chemical or physical interaction. The immobilization or attachment may be through a covalent bond using a specialty linker group. However, the immobilization need not be covalent or permanent.

The reaction components to perform methods of the invention can be delivered in a form of a kit. As used herein, the term "kit" refers to any system for delivering materials. In the context of reaction assays, such delivery systems include elements allowing the storage, transport, or delivery of reaction components such as oligonucleotides, buffering components, additives, reaction enhancers, enzymes and the like in the appropriate containers from one location to another commonly provided with written instructions for performing the assay. Kits may include one or more enclosures or boxes containing the relevant reaction reagents and supporting materials. The kit may comprise two or more separate containers wherein each of those containers includes a portion of the total kit components. The containers may be delivered to the intended recipient together or separately. In particular aspect, the kit to perform methods of the invention comprises at least one oligonucleotide probe incorporating at least one probe-anchoring modification. In other aspects, the kit can further incorporate an oligonucleotide primer incorporating a probe-anchoring modification. In additional aspects, the probe-anchoring modification comprises nucleotide sequence. The oligonucleotide probe of the kit can be a nuclease cleavable probe and the kit can be further comprising a nuclease wherein the nuclease can recognize and cleave the probe when the probe forms a complementary duplex. The probe can incorporate at least one duplex-stabilizing modification selected from minor groove binders, intercalators, duplex-stabilizing nucleotide analogs, and combinations thereof. In preferred aspects, the probe further comprises at least one detectable label. In yet another preferred embodiments, the detectable label comprises a fluorescent label. The fluorescent label preferably comprises two dyes that are in FRET interaction.

The oligonucleotide components of the invention such as primers and probes including those comprising PA modifications and PD sequences and other specialty oligonucleotides can be prepared by a suitable chemical synthesis method, including, for example, the phosphodiester method disclosed in Brown E. L. et al (1979), the phosphotriester method described in Narang S. A. et al (1979). The preferred approach is the diethylphosphoramidate method disclosed in Beaucage S. L., Caruthers M. H. (1981), in combination with the solid support method disclosed in Caruthers M. H., Matteucci M. D. (1984) and performed using one of commercial automated oligonucleotide synthesizer. When oligonucleotide components of the invention, for example the probes, need to be labeled with a fluorescent dye a wide range of fluorophores may be applied in designs and synthesis. Available fluorophores include but not limited to coumarin, fluorescein (FAM, usually 6-fluorescein or 6-FAM), tetrachlorofluorescein (TET), hexachloro fluorescein (HEX), rhodamine, tetramethyl rhodamine, BODIPY, Cy3, Cy5, Cy7, Texas red and ROX. Fluorophores may be chosen to absorb and emit in the visible spectrum or outside the visible spectrum, such as in the ultraviolet or infrared ranges. FRET probes of the invention commonly incorporate a pair of fluorophores, one of which may be a nonefluorescent chromophore (commonly referred as a "dark quencher"). Suitable dark quenchers described in the art include Dabcyl and its derivatives like Methyl Red. Commercial non-fluorescent quenchers, e.g., Eclipse™ (Glen Research) and BHQ1, BHQ2, BHQ3 (Biosearch Technologies), may be also used for synthesis of FRET probes of the invention. Preferred quenchers are either dark quenchers or fluorophores that do not fluoresce in the chosen detection range of the assays. The donor and acceptor fluorophores for manufacturing of the labeled oligonucleotide components of the invention may be selected from suitable fluorescent groups, e.g., 6-FAM (6-carboxyfluorescein); 6-hexachlorofluorescein ([4,7,2',4',5',7'-hexachloro-(3',6'-dipivaloylfluoresceinyl)-5-carboxylic acid]); 6-tetrachloro-fluorescein ([4,7,2',7'-tetrachloro-(3',6'-dipivaloylfluoresceinyl)-6-carboxylic acid]); 6-TAMRA (6-carboxytetramethylrhodamine; Dabcyl (4-((4-(dimethylamino)phenyl)azo) benzoic acid); Cy5 (Indodicarbocyanine-5); Cy3 (Indo-dicarbocyanine-3); and the like. Modified nucleoside or nucleotide analogs, for example, 5-bromouracil, 5-methyl cytosine, 5-iodo uracil, 2-amino adenosine (2,6-diaminopurine), 6-methyl adenosine, preudouridine, deoxyinosine and deoxyuridine, which are rarely present in natural nucleic acids may be incorporated synthetically into oligonucleotide components. The same applies to linkers, spacers, specialty tails like intercalators and minor groove binders. All these chemical components can be prepared according to methods of organic chemistry or using respective protocols that can be found in manuscripts and patents cited herein. Many structural modifications and modified nucleosides useful to prepare oligonucleotide components of the invention are available, commonly in convenient forms of phosphoramidites and specialty CPG, from commercial sources, e.g., Glen Research, Biosearch Technologies, etc.

Not unlike other detection technologies, the functional efficiency of probes and primers in methods of the invention depends, at least in part, on their hybridization properties. Hybridization properties of the primers and probes are primarily defined by their length, base composition and reaction conditions (e.g. magnesium ion concentration), etc. Duplex-stabilizing modifications can be effectively applied in the design, providing the primers and probes of the invention with enhanced hybridization properties. In particular aspects, hybridization properties of the primers and probes can be improved by amplifying target nucleic acids in the presence of base-modified duplex-stabilizing dNTPs. This technology has been described in detail (Kutyavin I. V., 2007b), which is incorporated herein by reference.

A simple estimate of the Tm value may be calculated using the equation $Tm=81.5+0.41(\% \text{ G+C})$, when a nucleic acid is in aqueous solution at 1 M NaCl. More accurate calculations can be made using the base pair thermodynamics of a "nearest-neighbors" approach (Breslauer K. J. et al, 1986; SantaLucia J. Jr., 1998). Commercial programs, including Oligo™, Primer Design and programs available on the internet like Primer3™ and Oligo Calculator™ can be also used to calculate a Tm of a nucleic acid sequence useful according to the invention. Commercial programs, e.g., Visual OMP™ (DNA software), Beacon designer 7.00™ (Premier Biosoft International), may also be helpful. However, these programs are usually made for the design of PCR primers and probes, and may not be suitable to incorporate all and/or different and numerous aspects of the invention. In a preferred embodiment, the probes and primers of the invention are designed using specialty computer software.

DNA polymerases and, in certain aspects, duplex-specific nucleases are key components in practicing detection assays of the invention. DNA polymerases useful according to the invention may be native polymerases as well as polymerase mutants, which are commonly modified to improve certain performance characteristics or to eliminate 5' to 3' and/or 3' to 5' exo/endo nuclease activities that may be found in many native enzymes. Nucleic acid polymerases can possess different degrees of thermostability. The choice of DNA polymerase to practice the methods of the invention depends on particular amplification technology used to produce the primer-extension or target amplification products. For example, to perform in the PCR methods, DNA polymerases should be stable at temperatures >90° C., preferably >95° C. and even more preferably >100° C. Examples of thermostable DNA polymerases which are useful for performing the PCR methods of the invention include but not limited to Pfu, Taq, Vent, Deep Vent and UlTma DNA polymerases and other polymerase from *Thermus* species or from *Thermotoga maritima*. Depending on the particular amplification technology, DNA polymerases may incorporate 5'→3' and 3'→5' "associated" nuclease activities. For example, Taq DNA polymerase from *Thermus aquaticus* has duplex-specific 5'-nuclease activity and this may be used in 5'-nuclease assays of the invention. JumpStart™ DNA polymerase from Sigma (antibody blocked Taq polymerase) was used in working Examples provided herein. The presence or absence in DNA polymerases of the 3'→5' nuclease activity, which is known in the art under the name "proofreading" nuclease activity, is not as significant for many methods of the invention as other characteristics such as the enzyme processivity, fidelity and DNA synthesis speed. The DNA polymerases used in certain methods of the invention, e.g. the methods of FIGS. 8A and 9, have preferably no "proofreading" nuclease activity. Mesophilic DNA polymerases like DNA polymerase I and Klenow Fragment of DNA polymerase I from *E. coli*, phi29 DNA polymerase, T4 and T7 DNA polymerases can be used at the reaction temperatures <50° C.

Particular methods of the invention are based on use of nuclease-cleavable probes. Generally, the same selection principals discussed for DNA polymerases apply to the duplex-specific nucleases. The nucleases of the invention recognize the probe:primer-extension duplex providing the probe cleavage and consequent detection of the cleaved products. The duplex-specific nucleases useful in practicing the invention do not substantially cleave oligonucleotide probes when they are in a single-stranded state and when they are not hybridized to the primer-extension products or target amplicons. Cleavage efficiency of duplex-specific nucleases of the invention in many occasions is significantly improved when yet another duplex structure appears in proximity of their cleavage site. This property of the endonucleases is used herein in cleaving the optimal cleavage structures. Examples of such structures are shown, for instance, in FIGS. 8C and 9F. Duplex-specific 5'-nuclease activities useful in practicing particular methods of the invention may be found in many DNA polymerases, e.g. *E. coli* DNA polymerase I and DNA polymerase isolated from *Therms aquaticus* (Taq), *Thermus thermophilus* (Tth), *Pyrococcus furiosus* (Pfu) and *Thermus flavus* (Tfl). As has been discussed herein, the 5'-duplex-specific activity can also be provided by 5'-flap endonucleases. The duplex-specific probe cleavage in methods of the invention can be also achieved using nucleases other than 5'-nuclease. The examples are illustrated in FIGS. 8B and 8C. Detailed teachings of nucleic acid detection based on duplex-specific Endonuclease IV activity can be found in Kutyavin I. V. et al, 2006 and 2007, which are incorporated herein by reference for their relevant teachings.

Methods of the invention may be performed in various reaction vessels or containers that may be made from any solid material, including but not limited to, plastic, glass, quartz, metal, etc. The reaction vessels may be of any size, wherein the reaction volume may be measured in nanoliter, microliter, milliliter or liter scales. The reaction vessels can be of any shape, e.g. tubes or plates wherein multiple reaction vessels are combined in one plate. The reaction vessels may be made from a liquid material wherein, for example, aqueous drops of the reaction mixtures of the invention are suspended and floating in oil. Methods of the invention may be performed in a micro-fluidic or fluidic card made from any material, usually plastic, and wherein the card comprises reaction chambers and channels allowing mixing the reaction components in an order or simultaneously as required by the methods of the invention.

DETAILED EXEMPLARY EMBODIMENTS

The following working Examples are provided and disclosed to demonstrate certain aspects and methods of the invention for detection of target nucleic acids. The examples are provided solely for illustrative purposes, and are not intended to limit the scope of the inventive methods and applications.

Example 1

Materials and Methods

Synthesis of Oligonucleotide Components.

Figure 10:
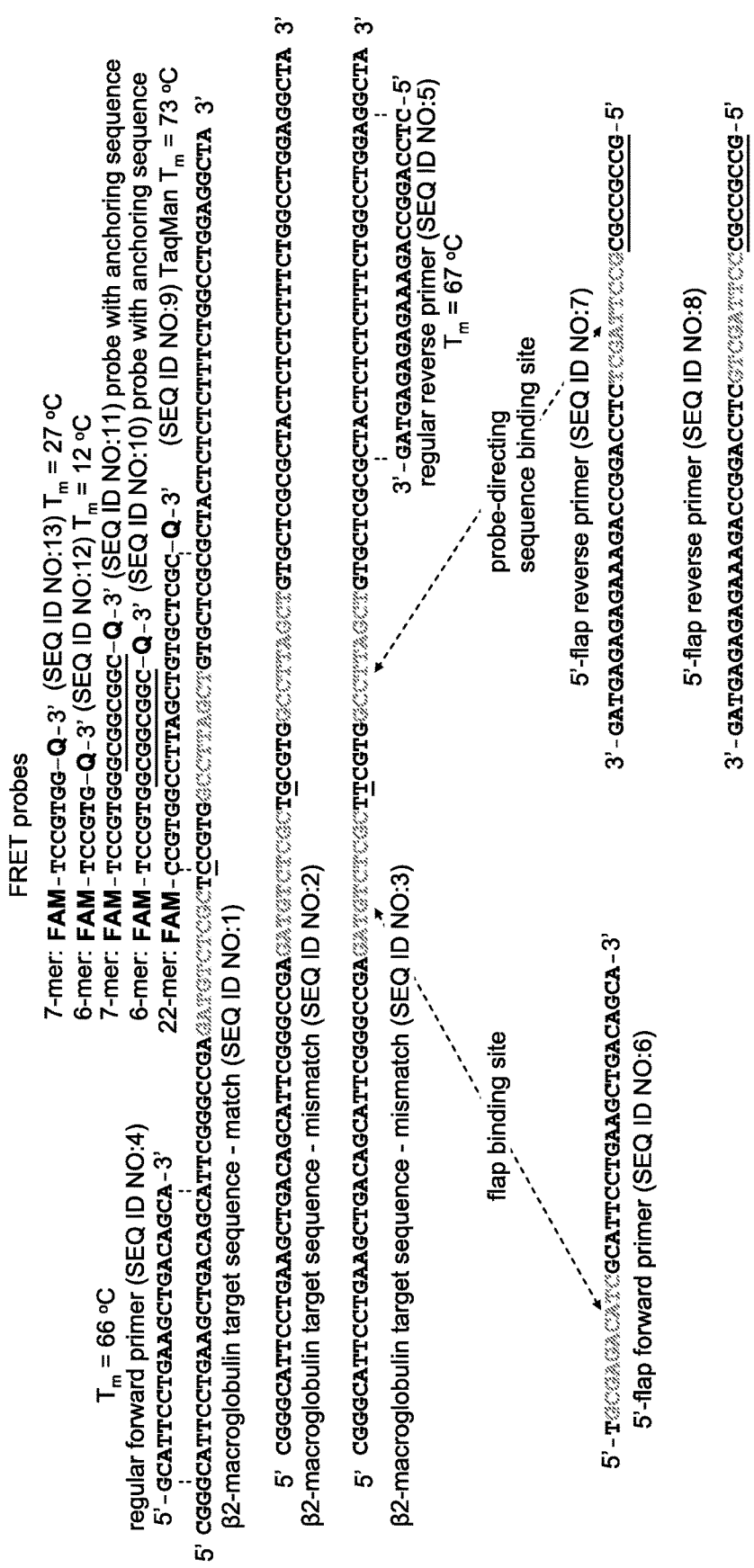
FIG. 10 shows, according to particular exemplary aspects of the present invention, three otherwise identical β2-macroglobulin target sequences (SEQ ID NO:1; SEQ ID NO:2; and SEQ ID NO:3), each with a different base at the underlined nucleotide. These target nucleotide sequences were detected using the listed PCR primers and FRET probes in the exemplary study. Wherever possible, the oligonucleotide sequences are aligned with the target DNA in the orientation (5'-to-3') as indicated. Regular forward primer (SEQ ID NO:4), regular reverse primer (SEQ ID NO:5) and a 22-mer FRET-probe (SEQ ID NO:9) were designed for the conventional Taqman™ assay whereas the 5'-flap forward primer (SEQ ID NO:6) and 5'-flap reverse primers (SEQ ID NO:7 and SEQ ID NO:8) were prepared for the target detection by methods of the invention. The 5'-flap reverse primer (SEQ ID NO:7) was designed to be used with a 6-mer FRET probe (SEQ ID NO:10) comprising a probe-anchoring sequence (underlined) whereas the 5'-flap reverse primer (SEQ ID NO:8) was used with a homologous 7-mer FRET probe (SEQ ID NO:11), respectively. Otherwise identical 6 and 7-mer FRET probes (SEQ ID NO:12 and SEQ ID NO:13, respectively), but lacking the probe-anchoring sequence were prepared and used in control experiments. The cleavage-enhancing and probe-directing sequences in the flap primers as well as their binding sites within the target sequence are marked in gray font. The probe-anchoring sequences are underlined. The melting temperatures ($T_m$'s) were calculated for a corresponding full complement duplex (200 nM) in 50 mM KCl, 2 mM MgCl$_2$, 20 mM Tris-HCl (pH 8.0). FAM is 6-fluorescein and Q is a dark quencher BHQ1 (Biosearch Technologies).

Structures and sequences of exemplary β2-macroglobulin target sequence which was detected using PCR primers and FRET probes are shown in FIG. 10. A 6-fluorescein reporting dye was incorporated onto the 5'-end of the probes, and a BHQ1 "dark" quencher was introduced to the 3'-end of the probes using respective phosphoramidite and CPG from Biosearch Technologies. Standard phosphoramidites, solid supports and reagents to perform the solid support oligonucleotide synthesis were purchased from Glen Research. 0.25 M 5-ethylthio-1H-tetrazile solution was used as a coupling agent. Oligonucleotides were synthesized either on ABI394 DNA synthesizer (Applied Biosystems) or MerMaid 6 DNA synthesizer (BioAutomation Corporation) using protocols recommended by the manufacturers for 0.2 μmole synthesis scales. After the automated synthesis, oligonucleotides were deprotected in aqueous 30% ammonia solution by incubation for 12 hours at 55° C. or 2 hours at 70° C.

Tri-ON oligonucleotides were purified by HPLC on a reverse phase C18 column (LUNA 5 μm, 100 A, 250×4.6 mm, Phenomenex Inc) using gradient of acetonitryl in 0.1 M triethyl ammonium acetate (pH 8.0) or carbonate (pH 8.5) buffer with flow rate of 1 ml/min. A gradient profile including washing stage 0→14% (10 sec), 14→45% (23 min), 45→90% (10 min), 90→90% (5 min), 90→0% (30 sec), 0→0% (7 min) was applied for purification of all Tri-ON oligonucleotides. The product containing fractions were dried down in vacuum (SPD 1010 SpeedVac, TermoSavant) and trityl groups were removed by treatment in 80% aqueous acetic acid at room temperature for 40-60 min. After addition to the detritylation reaction (100 µl) of 20 µl sodium acetate (3 M), the oligonucleotide components were precipitated in alcohol (1.5 ml), centrifuged, washed with alcohol and dried down. Concentration of the oligonucleotide components was determined based on the optical density at 260 nm and the extinction coefficients calculated for individual oligonucleotides using on-line OligoAnalyzer 3.0 software provided by Integrated DNA Technologies. Based on the measurements, convenient stock solutions in water were prepared and stored at −20° C. for further use. The purity of all prepared oligonucleotide components was confirmed by analytical 8-20% PAAG electrophoresis, reverse phase HPLC and by spectroscopy on Cary 4000 UV-VIS spectrophotometer equipped with Cary WinUV software, Bio Package 3.0 (Varian, Inc.).

Example 2

An Exemplary β2-Macroglobulin Target Sequence was PCR-Amplified and Detected in a Post-PCR Reaction Using 5'-Nuclease-Cleavable 6 and 7-mer FRET Probes Incorporating a Probe-Anchoring Sequence The detection reaction of the Example 2 was performed after the target amplification by PCR according to the method shown in FIG. 9. Reaction mixtures of 25 µl total volume were prepared to incorporate the following components with indicated providers, amounts and concentrations: 5'-flap forward primer (SEQ ID NO:6)—100 nM; 5'-flap reverse primer (SEQ ID NO:7) or (SEQ ID NO:8)—600 nM; 6-mer FRET probe (SEQ ID NO:10) or 7-mer FRET probe (SEQ ID NO:11)—200 nM; β2-macroglobulin target sequence (SEQ ID NO:1) or (SEQ ID NO:2) or (SEQ ID NO:3)—10,000 copies per reaction; dNTPs—200 µM each; JumpStart DNA polymerase (Sigma)—0.2 U/µl in 50 mM KCl, 5 mM MgCl$_2$, 20 mM Tris-HCl (pH 8.0). The 5'-flap reverse primer (SEQ ID NO:7) was used in reactions with the 6-mer FRET probe (SEQ ID NO:10) whereas 5'-flap reverse primer (SEQ ID NO:8) was used in the 7-mer FRET probe (SEQ ID NO:11) reactions. PCR profile comprised: incubation at 95° for 2 min (activation of the DNA polymerase) followed by 50 cycles of incubation at 95° for 10 sec and at 70° for 45 sec and then followed by incubation at a designated temperature X° C. for 30 min wherein fluorescence was monitored for 45 sec in every minute of the reaction time. The experiments were performed using SmartCycler™ (Cepheid). Initial fluorescence was subtracted.

Figure 11:
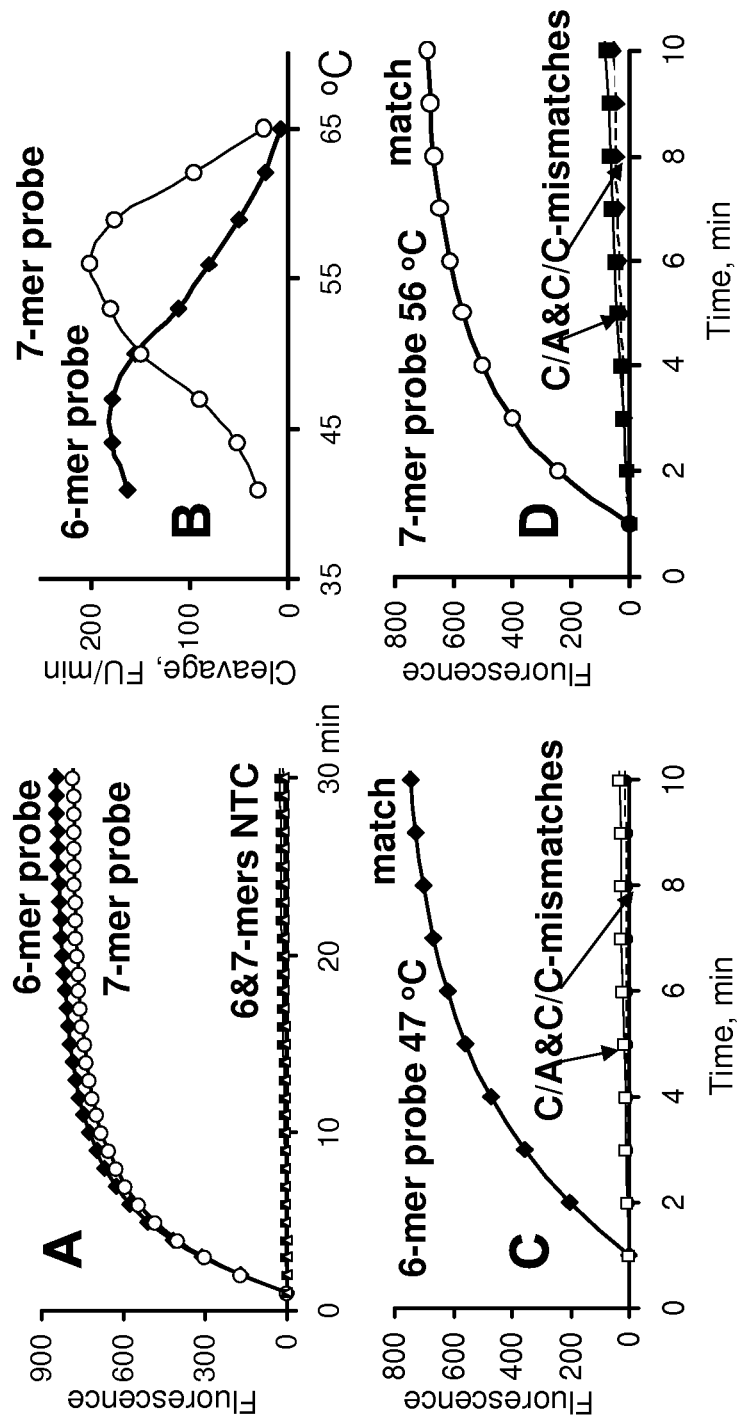
FIG. 11 shows, according to particular exemplary aspects of the present invention, results of detection of the β2-macroglobulin target sequences in a post-PCR assay using 6-mer (SEQ ID NO:10) and 7-mer (SEQ ID NO:11) FRET probes and conducted according to the reaction scheme illustrated in FIG. 9. In both cases, the target sequences were amplified using the 5'-flap forward primer (SEQ ID NO:6). The 5'-flap reverse primer (SEQ ID NO:7) was used in detection reactions with the 6-mer FRET probe (SEQ ID NO:10) whereas 5'-flap reverse primer (SEQ ID NO:8) was used with the 7-mer FRET probe (SEQ ID NO:11). The structures of the probes, primers and DNA targets are shown in FIG. 10. Detailed description of the experiments is provided herein in working Example 2.

Results of the experiments of Example 2 are shown in FIG. 11. In this set of experiments the target nucleic acid was first PCR-amplified and then detected at isothermal conditions. The experiments illustrate a method wherein all amplification and detection components are present in the reaction mixture and the division of the reaction on two consequent stages, amplification followed by detection, is achieved by the reaction temperature profile. PCR was performed at 70° C. and this temperature does not support the amplicon folding and therefore the probe binding. The detection reaction was triggered by lowering the reaction temperature <70° C. Specifically, FIG. 11A shows results of fluorescence monitoring at 50° C. (post-PCR detection stage) in detecting a β2-macroglobulin target sequence (SEQ ID NO:1) by 6-mer (SEQ ID NO:10) and 7-mer (SEQ ID NO:11) FRET probes, both of which incorporated a probe-anchoring sequence GCGGCGGC-3'. As can be seen in FIG. 11A, presence of the target nucleic acid in the reaction mixtures leads to rapid hydrolyses of both probes whereas no change in fluorescence was observed in absence of the target nucleic acid in the reaction mixture (NTC controls). In particular, these experiments (FIG. 11A) prove that the detection reaction is target-specific.

FIG. 11B shows results of the experiments wherein an optimal post-PCR detection temperature was identified for each of the 6-mer (SEQ ID NO:10) and 7-mer (SEQ ID NO:11) FRET probes in detecting the target sequence (SEQ ID NO:1). In these experiments, the designated detection temperature was ranging from 41° C. to 65° C. The initial rate of the cleavage in fluorescent units (FU) per minute was measured during the detection time when ~10-20% of the probe was cleaved and the cleavage rate results are plotted versus the detection temperature as indicated in FIG. 11B for each of the 6 and 7-mer probes. These experiments particularly showed that the probes have different temperatures for the optimal performance and these temperatures were 47° C. and 56° C. for 6 and 7-mer probe, respectively.

The optimal detection temperature conditions, 47° C. and 56° C. for 6 and 7-mer probes, respectively, determined in FIG. 11B were used in experiments of FIGS. 11C and 11D, wherein the probes were detecting the fully matched (SEQ ID NO:1) and two mismatched (SEQ ID NO:2 and SEQ ID NO:3) target sequences. The results of the FIGS. 11C and 11D indicate that both probes effectively discriminated a single nucleotide polymorphism. Specifically, the polymorphic targets resulting in C/A and C/C mismatched target-probe duplexes provided a barely detectable fluorescent signal in 10 minutes whereas the detection of the fully match matched target sequence (SEQ ID NO:1) resulted in complete probe hydrolysis. As anticipated, the shortest 6-mer probe was the most discriminatory.

Example 3

An Exemplary β2-Macroglobulin Target Sequence was PCR-Amplified and Detected in Real-Time Using 5'-Nuclease-Cleavable 6 and 7-mer FRET Probes Incorporating a Probe-Anchoring Sequence The detection reactions of the Example 3 were performed in real-time PCR, wherein the target amplification and detection were performed simultaneously. The reaction steps of the method are shown in FIG. 9. The results of the real-time fluorescence monitoring in detecting the target sequence (SEQ ID NO:1) by the 6 and 7-mer FRET probes (SEQ ID NO:10 and SEQ ID NO:11, respectively) are shown in FIGS. 12A and 12B. The reaction compositions were identical to those provided in working Example 2. PCR profile comprised incubation at 95° C. for 2 min (activation of the DNA polymerase) followed by 55 cycles incorporating three steps: (i) strand separation at 95° C. for 10 sec, (ii) detection at 56° C. for 70 sec and (iii) extension at 70° C. for 30 sec. The fluorescence data were collected during the extension step. Additionally, the same target sequence was detected in real time using a conventional, art recognized Taqman™ assay and the detection results are shown in FIG. 12C. The Taqman™ reaction mixtures of 25 µl A total volume were prepared to incorporate the following components with indicated providers, amounts and concentrations: regular forward (SEQ ID NO:4) and regular reverse (SEQ ID NO:5) primers—200 nM each; 22-mer FRET probe (SEQ ID NO:9)—200 nM; β2-macroglobulin target sequence (SEQ ID NO:1)—10,000 copies per reaction; dNTPs—200 µM each; JumpStart DNA polymerase (Sigma)—0.04 U/µl in 50 mM KCl, 5 mM MgCl$_2$, 20 mM Tris-HCl (pH 8.0). The Taqman™ PCR profile comprised: incubation at 95° C. for 2 min (activation of the DNA polymerase) followed by 55 cycles of incubation at 95° C. for 10 sec and at 68° C. for 45 sec. The reaction fluorescence was monitored at the combined annealing/extension stage (68° C.). The experiments were performed on SmartCycler™ (Cepheid) and initial fluorescence was subtracted using the instrument software.

A number of control experiments were conducted to emphasize the unique mechanism of the invention methods which allows, in particular, the use of exceptionally short FRET probes in real time PCR (see FIGS. 12A and 12B). For example, when the 6 and 7-mer FRET probes incorporating the probe-anchoring sequence (SEQ ID NO:10 and SEQ ID NO:11, respectively) were replaced, in otherwise identical reactions, by the conventionally designed probes of the same length and composition but lacking the probe-anchoring sequence (SEQ ID NO:12 and SEQ ID NO:13), no fluorescence signal was detected. The control experiments also prove that formation of both stem-loop structures illustrated in FIG. 9E is important to enable the 6 and 7-mer FRET probes (SEQ ID NO:10 and SEQ ID NO:11) to provide the detectable real-time signal which is nearly identical in strength to that provided by the art recognized Taqman™ assay employing relatively long, 22-mer FRET probe (SEQ ID NO:9) (see FIGS. 12A and 12B and 12C). For example, low fluorescence or no signal was observed in the control experiments wherein, in otherwise identical reactions, one of the 5'-flap primers (SEQ ID NO:6, 7 or 8) was replaced by a regular forward (SEQ ID NO:4) or regular reverse (SEQ ID NO:5) primer.

The conventional 6 and 7-mer probes lacking the anchoring sequence (SEQ ID NO:12 and SEQ ID NO:13) have melting temperatures of 12° C. and 27° C., respectively. Not surprisingly, the probes with such low hybridization properties do not perform in conventional assay. The observed probe stabilization provided by the probe-anchoring approach of the invention was unexpectedly so strong as it induced these probes to form stable duplexes with the target amplicons at the elevated PCR temperature of 56° C.

Example 4

Real Time PCR Detection of Single Nucleotide Variations in an Exemplary β2-Macroglobulin Target Sequence Using 5'-Nuclease-Cleavable 6 and 7-mer FRET Probes Incorporating a Probe-Anchoring Sequence The instant working Example 2 illustrates methods of the invention for detection of polymorphic variations in a post-PCR format. The present Example 4 demonstrates the use of the invention for the same purpose but in a preferred real time format. The reaction steps of the method are shown in FIG. 9. The results of the real time fluorescence monitoring in detecting the polymorphic target sequences (SEQ ID NO:1; SEQ ID NO:2; and SEQ ID NO:3) by the 6 and 7-mer FRET probes (SEQ ID NO:10 and SEQ ID NO:11, respectively) are shown in FIGS. 13A and 13B. Except the target variations, the reaction compositions and PCR profile were identical to those described in Example 3 experiments. The structures of the probes, primers and DNA targets are shown in FIG. 10.

Specifically, the results provided in FIGS. 13A and 13B show that the 6 and 7-mer FRET probes completely discriminates the target sequence variations as small as single nucleotide polymorphism. Excellent fluorescence signal was observed for both probes in case of the match target sequence (SEQ ID NO:1) whereas the mismatched target sequences provided an extremely low signal (e.g., C/A-mismatch in FIG. 13B) or no signal at all. The shortest timer probe was the most discriminatory (FIG. 13A), and overall discrimination in the real-time experiments was similar, if not better than that observed for the same probes used in the post-PCR detection format (see FIGS. 11C and 11D).

REFERENCES CITED, AND INCORPORATED HEREIN BY REFERENCE THERETO FOR THEIR RESPECTIVE TEACHINGS

Afonina I. A. et al (2002) *BioTechniques*, V.32, 940-949.
An L. et al (2005) *JBC*, V.280, 28952-28958.
Asseline U. et al (1984) *Proc. Natl. Acad. Sci. USA*, V.81, 3297-3301.
Ausubel F. M et al, eds. (1993) *Current Protocols in Molecular Biology*, Vol. 1, Chapter 2, Section I, John Wiley & Sons, New York.
Beaucage S. L., Caruthers M. H. (1981) *Tetrahedron Lett.*, V.22, 1859-1862.
Benner S. A. (2000) U.S. Pat. No. 6,140,496.
Boom W. R., Henriette M. A., Kievits T., Lens P. F. (1993) U.S. Pat. No. 5,234,809.
Breslauer K. J. et al (1986) *Proc. Natl. Acad. Sci. USA*, V.83, 3746-3750.
Brown E. L. et al (1979) *Methods Enzymol.*, V.68, 109-151.
Caruthers M. H., Matteucci M. D. (1984) U.S. Pat. No. 4,458,066.
Cleuziat P. and Mandrand B. (1998) U.S. Pat. No. 5,824,517.
Dahlberg J. E., Lyamichev V. I., Brow M. A. D. (1995) U.S. Pat. No. 5,422,253.
Dahlberg J. E., Lyamichev V. I., Brow M. A. D. (1997) U.S. Pat. No. 5,691,142.
Dahlberg J. E., Lyamichev V. I., Brow M. A. D. (1998) U.S. Pat. No. 5,837,450.
Davey C. and Malek L. T. (2000) U.S. Pat. No. 6,063,603.
Didenko V. V. (2001) *BioTechniques*, V.31, 1106-1121.
Duck P., Bender R., Crosby W., Robertson J. G. (1989) U.S. Pat. No. 4,876,187.
Duck, P., Bender, R. (1991) U.S. Pat. No. 5,011,769.
Eckstein F., ed., (1991) *Oligonucleotides and Analogs: A Practical Approach*. Oxford University Press, New York.
Eftink M. R. (1991) Fluorescence quenching: theory and applications. In Lakowicz J. R. (ed.), *Topics in Fluorescence Spectroscopy*. Plenum Press, New York, V.2: 53-126.
Egholm M. et al (1993) *Nature*, V.365, 566-568.
Fong W. et al (2000) *J. Clin. Microbiol.*, V.38, 2525-2529.
Förster T. (1965) Delocalized excitation and excitation transfer. In Sinanoglu, O. (ed.), *Modern Quantum Chemistry, Istanbul Lectures, part III*. Academic Press, New York, 93-137.
Fraiser M. S. et al (1997) U.S. Pat. No. 5,648,211.
Gait M. J., ed., (1984) *Oligonucleotide Synthesis: A Practical Approach*, IRL Practical Approach Series, IRL Press, Oxford.
Gelfand D. H., Holland P. M., Saiki R. K., Watson R. M. (1993) U.S. Pat. No. 5,210,015.
Gelfand D. H., Holland P. M., Saiki R. K., Watson R. M. (1996) U.S. Pat. No. 5,487,972.

Harvey J. J. et al (2004) *Anal. Biochem.*, V.333, 246-255.

Heller M. J. and Morrison L. E. (1985) Chemiluminescent and fluorescent probes for DNA hybridization. In Kingsbury, D. T. and Falkow, S. (eds.), *Rapid Detection and Identification of Infectious Agents*. Academic Press, New York, 245-256.

Kornberg A., and Baker T. (1992) *DNA Replication*, Second Edition, W. H. Freeman and Company, New York.

Kurn N. (2001) U.S. Pat. No. 6,251,639.

Kutyavin I. V., Lukhtanov E. A., Gamper H. B., Meyer Jr., R. B. (1998) U.S. Pat. No. 5,801,155.

Kutyavin I. V. et al (2006) *Nucleic Acids Res.*, V.34, e128.

Kutyavin I. V., Milesi D., Hoekstra M. F. (2007) U.S. Pat. No. 7,252,940.

Kutyavin I. V. (2007a) PCT patent application, WO/2007/127999.

Kutyavin I. V. (2007b) PCT patent application, WO/2007/127992.

Kutyavin I. V. (2009) PCT patent application, WO/2009/042291.

Lebedev Y. et al (1996) *Genet. Anal.*, V.13, 15-21.

Lehninger A. L. (1975) *Biochemistry*, 2nd edition. New York, Worth Publishers, Inc.

Livak K. J., Flood S. J. A., Marmaro J. and Mullah K. B. (1998) U.S. Pat. No. 5,723,591.

Lizardi P. M. et al (1992) U.S. Pat. No. 5,118,801.

Lizardi P. (1998) U.S. Pat. No. 5,854,033.

Lizardi P. (2001) U.S. Pat. No. 6,210,884.

Lyamichev V. et al (1993) *Science*, V.260, 778-783.

Mackay I. M. et al (2002) *Nucleic Acids Res.*, V.30, 1292-1305.

Mackay J., Landt O. (2007) *Methods Mol. Biol.*, V.353, 237-262.

McPherson M. J. et al, eds (1991) *PCR: A Practical Approach*. IRL Press, Oxford.

McPherson M. J. et al, eds (1995) *PCR2: A Practical Approach*. IRL Press, Oxford.

Millar D. S., Melki J. R., Grigg G. W. (2006) PCT patent application, WO 2006/125267.

Miller S. A., Dykes D. D., Polesky H. F. (1988) *Nucleic Acids Res.*, V.16, 1215.

Mullis K. B. (1987) U.S. Pat. No. 4,683,202.

Mullis K. B. et al (1987) U.S. Pat. No. 4,683,195.

Narang S. A., Hsiung H. M., Brousseau R. (1979) *Methods Enzymol.*, V.68, 90-98.

Nelson J. R. et al (2008) PCT patent application, WO/2008/086381.

Notomi T., Hase T. (2002) U.S. Pat. No. 6,410,278.

Oehlenschlager F. et al (1996) *Proc. Natl. Acad. Sci. USA*, V.93, 12811-12816.

Robelek R., Niu L., Schmid E. L., Knoll W. (2004) *Anal. Chem.*, V.76, 6160-6165.

Sagawa H. et al (2003) European Patent Application 1312682.

Sambrook J., Fritsch E. F. and Maniatis T. (1989) *Molecular Cloning: A Laboratory Manual*, 2nd Edition. Cold Spring Harbor Lab. Cold Spring Harbor, N.Y.

SantaLucia J. Jr. (1998) *Proc. Natl. Acad. Sci. USA*, V.95, 1460-1465.

Van Ness J. et al (2003a) *Proc. Natl. Acad. Sci. USA*, V.100, 4504-4509.

Van Ness J. et al (2003b) US Patent Application Publication 2003/0138800.

Vincent M., Xu Y. and Kong H. (2004) *EMBO reports*, V.5, 795-800.

Walder J. A., Walder R. Y. (1995) U.S. Pat. No. 5,403,711.

Walker G. T. (1998) U.S. Pat. No. 5,712,124.

Walker G. T., Linn C. P. and Nadeau J. G. (1996) *Nucleic Acids Res.*, V.24, 384-353.

Walker G. T., Little M. C., and Nadeau J. G. (1993) U.S. Pat. No. 5,270,184.

Walsh P. S., Metzger D. A., and Higuchi R. (1991) *Biotechniques*, V.10, 506-513.

Wengel J., Nielsen P. (2003) U.S. Pat. No. 6,670,461.

The invention claimed is:

1. A method of detecting a target nucleic acid in a test sample, comprising:

providing a reaction mixture comprising a target nucleic acid having a respective target nucleic acid sequence, an oligonucleotide primer complementary to the target nucleic acid sequence and having at least one 5' probe-anchoring nucleotide sequence and additionally having a probe-directing sequence complementary to a nucleotide sequence of a primer extension product, wherein the probe-directing sequence prompts the primer extension product to fold into a stem-loop structure with the probe-anchoring nucleotide sequence spatially proximate to the stem of the stem-loop, wherein the stem comprises the probe-directing sequence and the primer-extension product duplex, and a DNA polymerase suitable for primer extension;

incubating the reaction mixture in the presence of suitable reagents and under reaction conditions suitable to support primer hybridization and DNA polymerase-mediated primer extension and amplification to produce primer extension products incorporating the 5' probe anchoring sequence and its complement;

rendering the primer-extension products single stranded;

providing, in the reaction mixture, at least one oligonucleotide probe comprising a probe-anchoring nucleotide sequence complementary to the primer 5' probe-anchoring nucleotide sequence or to its complement, and wherein the probe hybridizes to the primer extension product or to its complement;

incubating the reaction mixture to hybridize the probe to the primer extension product or to its complement to provide a stabilized duplex; and detecting the duplex, wherein the presence of the duplex is indicative of the presence of the target nucleic acid sequence in the reaction mixture.

2. The method of claim 1, comprising:

providing a plurality of target nucleic acids and a plurality of oligonucleotide primers complementary to the target nucleic acid sequence, each oligonucleotide primer having at least one 5' probe-anchoring nucleotide sequence and additionally having a probe-directing sequence complementary to a nucleotide sequence of a primer extension product, wherein the probe-directing sequence prompts the primer extension product to fold into a stem-loop structure with the probe-anchoring nucleotide sequence spatially proximate to the stem of the stem-loop, wherein the stem comprises the probe-directing sequence; and providing a plurality of oligonucleotide probes, each oligonucleotide probe comprising a probe-anchoring nucleotide sequence complementary to the primer 5' probe-anchoring nucleotide sequence or to its complement, and wherein the probe hybridizes to the primer extension product or to its complement; and detecting the duplexes.

3. The method of claim 1, wherein the oligonucleotide primer comprises at its 5'-end at east one 5' probe-anchoring nucleotide sequence, wherein the at least one oligonucleotide probe comprises at its 3'-end a 3' probe-anchoring sequence, and wherein the at least one oligonucleotide probe hybridizes to the primer extension product.

4. The method of claim 1, wherein detecting the duplex comprises providing a nuclease to cleave the oligonucleotide probe hybridized to the target amplicon of the duplex so as to generate cleavage products, and wherein further detecting the presence of at least one of the cleavage products is indicative of the presence of the target nucleic acid sequence in the test sample.

5. The method of claim 4, wherein the probe cleavage is performed in a cycling mode.

6. The method of claim 4, wherein the nuclease is selected from Endonuclease IV, Endonuclease V or 5'-nuclease.

7. The method of claim 1, wherein the at least one 5' probe-anchoring nucleotide sequence comprises at least one nucleotide analog.

8. The method of claim 1, wherein the target nucleic acid is amplified by a PCR amplification or an isothermal amplification.

9. The method of claim 1, wherein the detection reaction is performed after the amplification reaction.

10. The method of claim 1, wherein the amplification and detection reactions are performed simultaneously, in real time.

11. The method of claim 1, wherein the target nucleic acid sequence is DNA or RNA, and wherein detecting the target nucleic acid comprises detecting DNA and or cDNA.

12. The method of claim 1, further comprising determining the amount of the target nucleic acid in or from the sample.

13. The method of claim 1, wherein the probe further comprises a detectable label.

14. The method of claim 13, wherein the detectable label comprises a fluorescent label.

15. The method of claim 14, wherein the fluorescent label comprises two dyes that are in FRET interaction, and wherein duplex formation disrupts FRET resulting in a detectable signal.

16. The method of claim 1, wherein at least one of the target nucleic acid, primer, primer extension product and or probe is immobilized on a solid support.

17. The method of claim 1, wherein the at least one probe is no longer ten than nucleotides.

18. The method of claim 1, wherein the oligonucleotide primer comprises at its 5'-end at least one 5' probe-anchoring nucleotide sequence, wherein the primer provides for an amplification product having at its 3'-end a 3' probe-anchoring sequence that is complementary to the 5' probe-anchoring nucleotide sequence of the primer, and wherein the probe comprises a 5' nucleotide sequence that is complementary and hybridizes to the 3' probe-anchoring sequence of the amplification product.

* * * * *

SEQUENCE LISTING

```
<160> NUMBER OF SEQ ID NOS: 13

<210> SEQ ID NO 1
<211> LENGTH: 96
<212> TYPE: DNA
<213> ORGANISM: Homo sapiens

<400> SEQUENCE: 1
cgggcattcc tgaagctgac agcattcggg ccgagatgtc tcgctccgtg gccttagctg     60
tgctcgcgct actctctctt tctggcctgg aggcta                              96

<210> SEQ ID NO 2
<211> LENGTH: 96
<212> TYPE: DNA
<213> ORGANISM: Homo sapiens

<400> SEQUENCE: 2
cgggcattcc tgaagctgac agcattcggg ccgagatgtc tcgctgcgtg gccttagctg     60
tgctcgcgct actctctctt tctggcctgg aggcta                              96

<210> SEQ ID NO 3
<211> LENGTH: 96
<212> TYPE: DNA
<213> ORGANISM: Homo sapiens
```

-continued

<400> SEQUENCE: 3
cgggcattcc tgaagctgac agcattcggg ccgagatgtc tcgcttcgtg gccttagctg    60
tgctcgcgct actctctctt tctggcctgg aggcta                              96

<210> SEQ ID NO 4
<211> LENGTH: 21
<212> TYPE: DNA
<213> ORGANISM: Artificial Sequence
<220> FEATURE:
<223> OTHER INFORMATION: forward primer for beta-2 macroglobulin

<400> SEQUENCE: 4
gcattcctga agctgacagc a                                              21

<210> SEQ ID NO 5
<211> LENGTH: 24
<212> TYPE: DNA
<213> ORGANISM: Artificial Sequence
<220> FEATURE:
<223> OTHER INFORMATION: beta-2 macroglobulin reverse primer (regular)

<400> SEQUENCE: 5
ctccaggcca gaaagagaga gtag                                           24

<210> SEQ ID NO 6
<211> LENGTH: 32
<212> TYPE: DNA
<213> ORGANISM: Artificial Sequence
<220> FEATURE:
<223> OTHER INFORMATION: beta-2 macroglobulin forward primer flap

<400> SEQUENCE: 6
tgcgagacat cgcattcctg aagctgacag ca                                  32

<210> SEQ ID NO 7
<211> LENGTH: 41
<212> TYPE: DNA
<213> ORGANISM: Artificial Sequence
<220> FEATURE:
<223> OTHER INFORMATION: beta-2 macroglobulin flap reverse primer

<400> SEQUENCE: 7
gccgccgcgc cttagctctc caggccagaa agagagagta g                        41

<210> SEQ ID NO 8
<211> LENGTH: 41
<212> TYPE: DNA
<213> ORGANISM: Artificial Sequence
<220> FEATURE:
<223> OTHER INFORMATION: beta-2 macroglobulin flap reverse primer 2

<400> SEQUENCE: 8
gccgccgccc ttagctgctc caggccagaa agagagagta g                        41

<210> SEQ ID NO 9
<211> LENGTH: 7
<212> TYPE: DNA
<213> ORGANISM: Artificial Sequence
<220> FEATURE:
<223> OTHER INFORMATION: beta-2 macroglobulin FRET probe 1

<400> SEQUENCE: 9 tccgtgg                                                              7

```
<210> SEQ ID NO 10
<211> LENGTH: 6
<212> TYPE: DNA
<213> ORGANISM: Artificial Sequence
<220> FEATURE:
<223> OTHER INFORMATION: beta-2 macroglobulin FRET probe 2

<400> SEQUENCE: 10 tccgtg                                                                 6

<210> SEQ ID NO 11
<211> LENGTH: 15
<212> TYPE: DNA
<213> ORGANISM: Artificial Sequence
<220> FEATURE:
<223> OTHER INFORMATION: beta-2 macroglobulin FRET probe 3

<400> SEQUENCE: 11
tccgtgggcg gcggc                                                      15

<210> SEQ ID NO 12
<211> LENGTH: 14
<212> TYPE: DNA
<213> ORGANISM: Artificial Sequence
<220> FEATURE:
<223> OTHER INFORMATION: beta-2 macroglobulin FRET probe 4

<400> SEQUENCE: 12
tccgtggcgg cggc                                                       14

<210> SEQ ID NO 13
<211> LENGTH: 22
<212> TYPE: DNA
<213> ORGANISM: Artificial Sequence
<220> FEATURE:
<223> OTHER INFORMATION: beta-2 macroglobulin FRET probe 5

<400> SEQUENCE: 13
ccgtggcctt agctgtgctc gc                                              22
```